(12) United States Patent
Schuman et al.

(10) Patent No.: US 10,507,036 B2
(45) Date of Patent: Dec. 17, 2019

(54) TISSUE-REMOVING CATHETER, TISSUE-REMOVING ELEMENT, AND METHOD OF MAKING SAME

(71) Applicant: Covidien LP, Mansfield, MA (US)

(72) Inventors: Victoria Schuman, Minneapolis, MN (US); Ethan Guggenheimer, Minnetonka, MN (US)

(73) Assignee: Covidien LLP, Mansfield, MA (US)

( * ) Notice: Subject to any disclaimer, the term of this patent is extended or adjusted under 35 U.S.C. 154(b) by 415 days.

(21) Appl. No.: 14/994,343

(22) Filed: Jan. 13, 2016

(65) Prior Publication Data

US 2017/0196588 A1    Jul. 13, 2017

(51) Int. Cl.
*A61B 17/3207*    (2006.01)
*A61B 17/3205*    (2006.01)

(52) U.S. Cl.
CPC ........ *A61B 17/320758* (2013.01); *A61B 17/32053* (2013.01); *A61B 17/320783* (2013.01); *A61B 2017/320775* (2013.01); *A61B 2017/320791* (2013.01)

(58) Field of Classification Search
CPC ...... A61B 17/320758; A61B 17/00234; A61B 17/32053; A61B 17/320783; A61B 2017/00292; A61B 2017/320775; A61B 2017/320791
See application file for complete search history.

(56) References Cited

U.S. PATENT DOCUMENTS

| | | |
|---|---|---|
| 4,418,589 A | 12/1983 | Cowart, Sr. |
| 4,765,332 A | 8/1988 | Fischell et al. |
| 4,925,216 A | 5/1990 | Steer |
| 5,044,838 A | 9/1991 | Brookfield |
| 5,084,010 A | 1/1992 | Plaia et al. |
| 5,156,071 A | 10/1992 | Stevens |
| 5,351,595 A | 10/1994 | Johnston |
| 5,366,464 A | 11/1994 | Belknap |
| 5,507,760 A | 4/1996 | Wynne et al. |
| 5,562,694 A | 10/1996 | Sauer et al. |
| 5,651,781 A | 6/1997 | Grace |

(Continued)

FOREIGN PATENT DOCUMENTS

| | | |
|---|---|---|
| EP | 0 286 334 A3 | 10/1988 |
| EP | 1 058 516 B1 | 12/2000 |

(Continued)

*Primary Examiner* — Kathleen S Holwerda
*Assistant Examiner* — Brooke Labranche

(57) ABSTRACT

A tissue-removing catheter includes a tissue-removing element operatively connected to a drive shaft for rotation of the tissue-removing element about an axis of rotation in a cutting direction. In some embodiments, the tissue removing element has a cutting blade and cutting teeth positioned radially inward of the cutting blade with respect to the axis of rotation. The cutting blade and cutting teeth are fixed with respect to one another to form first and second cuts in tissue as the tissue-removing element rotates. In certain embodiments, the tissue-removing element includes a cutting blade and raised elements spaced apart inward of the cutting blade relative to the axis of rotation to define an annular tissue-receiving channel between the cutting blade and the raised elements. A bottom surface of the channel can define cutting teeth.

11 Claims, 18 Drawing Sheets

(56) References Cited

U.S. PATENT DOCUMENTS

| | | |
|---|---|---|
| 5,653,560 A | 8/1997 | Weber et al. |
| 5,904,679 A | 5/1999 | Clayman |
| 5,919,203 A | 7/1999 | Husted et al. |
| 5,925,056 A | 7/1999 | Thomas et al. |
| 6,136,014 A | 10/2000 | Sirimanne et al. |
| 6,451,036 B1 | 9/2002 | Heitzmann et al. |
| 6,537,287 B1 | 3/2003 | Yencho et al. |
| 6,623,496 B2 | 9/2003 | Snow et al. |
| 6,666,874 B2 | 12/2003 | Heitzmann et al. |
| 6,685,707 B2 | 2/2004 | Roman et al. |
| 6,746,451 B2 | 6/2004 | Middleton et al. |
| 6,997,934 B2 | 2/2006 | Snow et al. |
| 7,171,798 B1 | 2/2007 | Bemardy |
| 7,172,610 B2 | 2/2007 | Heitzmann et al. |
| 7,563,267 B2 | 7/2009 | Goldfarb et al. |
| 7,655,015 B2 | 2/2010 | Goldfarb et al. |
| 7,666,134 B2 | 2/2010 | Ericksson et al. |
| 7,736,388 B2 | 7/2010 | Goldfarb et al. |
| 7,842,058 B2 | 10/2010 | Simpson et al. |
| 8,057,493 B2 | 11/2011 | Goldfarb et al. |
| 8,062,300 B2 | 11/2011 | Schmitz et al. |
| 8,070,762 B2 | 12/2011 | Escudero et al. |
| 8,142,463 B2 | 3/2012 | Arcenio et al. |
| 8,192,435 B2 | 6/2012 | Bleich et al. |
| 8,215,533 B2 | 7/2012 | Viola et al. |
| 8,236,016 B2 | 8/2012 | To et al. |
| 8,262,585 B2 | 9/2012 | Thompson et al. |
| 8,298,252 B2 | 10/2012 | Krolik et al. |
| 8,308,746 B2 | 11/2012 | Pravong et al. |
| 8,337,516 B2 | 12/2012 | Escudero et al. |
| 8,361,094 B2 | 1/2013 | To et al. |
| 8,468,919 B2 | 6/2013 | Christian et al. |
| 8,469,981 B2 | 6/2013 | Robertson et al. |
| 8,475,483 B2 | 7/2013 | Schmitz et al. |
| 8,500,761 B2 | 8/2013 | Goldfarb et al. |
| 8,531,064 B2 | 9/2013 | Robertson et al. |
| 2002/0077642 A1 | 6/2002 | Patel et al. |
| 2002/0082592 A1 | 6/2002 | Lary |
| 2002/0184980 A1 | 12/2002 | Fasnacht et al. |
| 2004/0035274 A1 | 2/2004 | Fasnacht et al. |
| 2007/0129675 A1 | 6/2007 | Summersville et al. |
| 2007/0266833 A1 | 11/2007 | Radziszewski et al. |
| 2008/0312681 A1 | 12/2008 | Ansel et al. |
| 2009/0019826 A1 | 1/2009 | Rigney |
| 2010/0139465 A1 | 6/2010 | Christian et al. |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2011/0054507 A1 | 3/2011 | Batten et al. |
| 2011/0098711 A1 | 4/2011 | Batten et al. |
| 2012/0022564 A1 | 1/2012 | Batten et al. |
| 2012/0046679 A1 | 2/2012 | Patel et al. |
| 2012/0296277 A1 | 11/2012 | Summersville et al. |
| 2013/0096587 A1 | 4/2013 | Smith et al. |
| 2014/0128893 A1* | 5/2014 | Guggenheimer ......................... A61B 17/320758 606/159 |
| 2014/0222046 A1* | 8/2014 | Schneider ...... A61B 17/320758 606/159 |

FOREIGN PATENT DOCUMENTS

| | | |
|---|---|---|
| EP | 1 158 910 B1 | 12/2001 |
| EP | 1 870 044 B1 | 12/2007 |
| EP | 1 957 134 B1 | 8/2008 |
| WO | 88/00458 A1 | 1/1988 |
| WO | 2007/067449 A2 | 6/2007 |
| WO | 2007/095751 A1 | 8/2007 |
| WO | 2008/157202 A1 | 12/2008 |
| WO | 2010/009093 A2 | 1/2010 |
| WO | 2010/077692 A2 | 7/2010 |
| WO | 2010/115163 A9 | 10/2010 |
| WO | 2010/121172 A1 | 10/2010 |
| WO | 2012/003430 A2 | 1/2012 |
| WO | 2013/049734 A1 | 4/2013 |

\* cited by examiner

TISSUE-REMOVING CATHETER, TISSUE-REMOVING ELEMENT, AND METHOD OF MAKING SAME

FIELD OF THE DISCLOSURE

The present disclosure generally relates to a tissue-removing catheter, tissue-removing element thereof, and method of making the tissue-removing element.

BACKGROUND OF THE DISCLOSURE

Tissue removing catheters are used to remove unwanted tissue from the body. As an example, atherectomy catheters are used to remove material from a blood vessel to open the blood vessel and improve blood flow through the vessel.

SUMMARY OF THE DISCLOSURE

A tissue-removing catheter includes a tissue-removing element operatively connected to a drive shaft for rotation of the tissue-removing element about an axis of rotation in a cutting direction. In some embodiments, the tissue removing element has a cutting blade and cutting teeth positioned radially inward of the cutting blade with respect to the axis of rotation. The cutting blade and cutting teeth are fixed with respect to one another to form first and second cuts in tissue as the tissue-removing element rotates. In certain embodiments, the tissue-removing element includes a cutting blade and raised elements spaced apart inward of the cutting blade relative to the axis of rotation to define an annular tissue-receiving channel between the cutting blade and the raised elements. A bottom surface of the channel can define cutting teeth.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
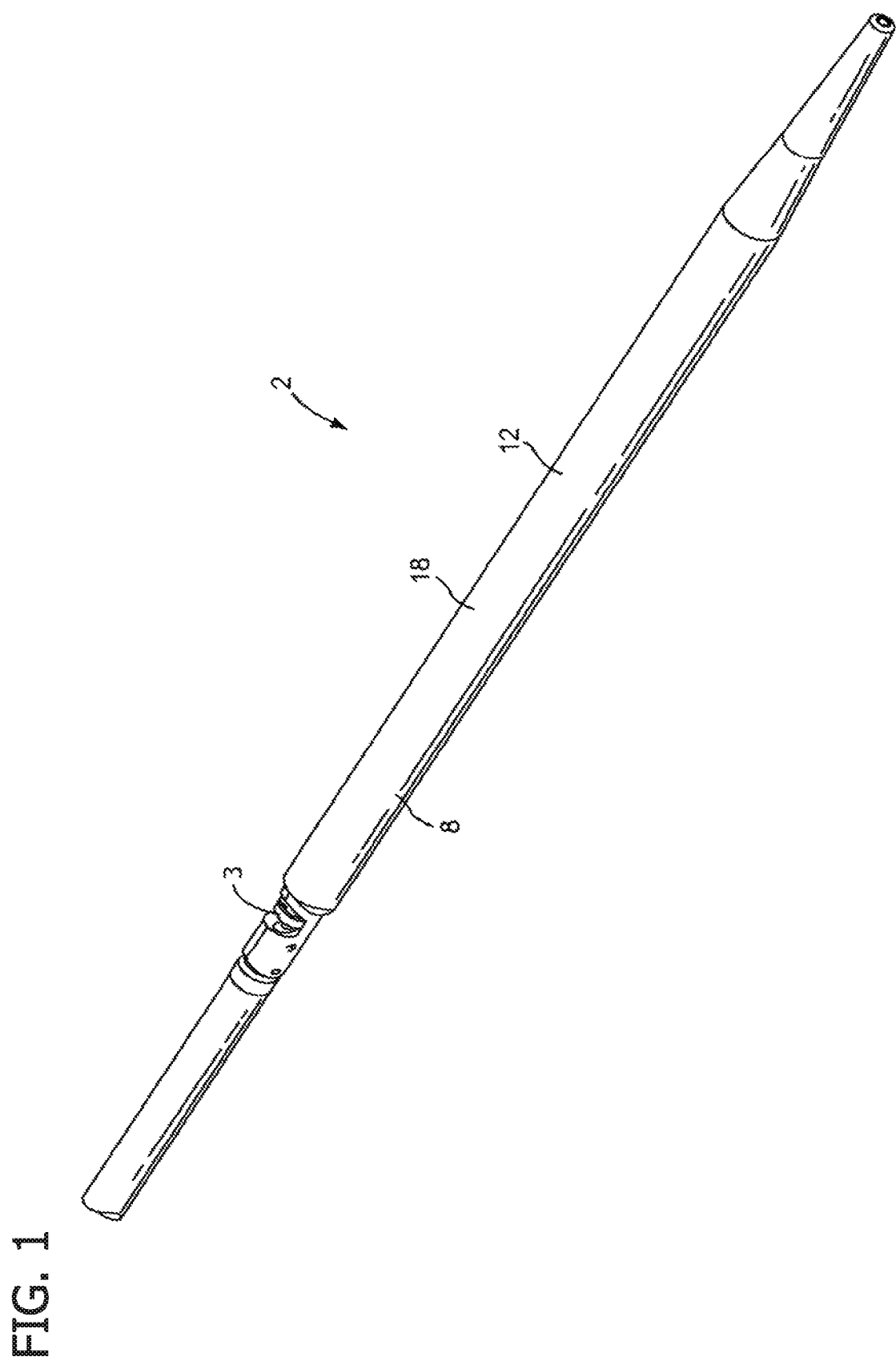
FIG. 1 is a perspective of a distal end of an atherectomy catheter.

Referring now to the drawings, several embodiments of a tissue-removing catheter for removing tissue from a body lumen are disclosed. In particular, the illustrated catheter embodiments are suitable for removing tissue from a body lumen wall, and are particularly suitable for removing (i.e., excising) plaque tissue from a vessel wall (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 2:
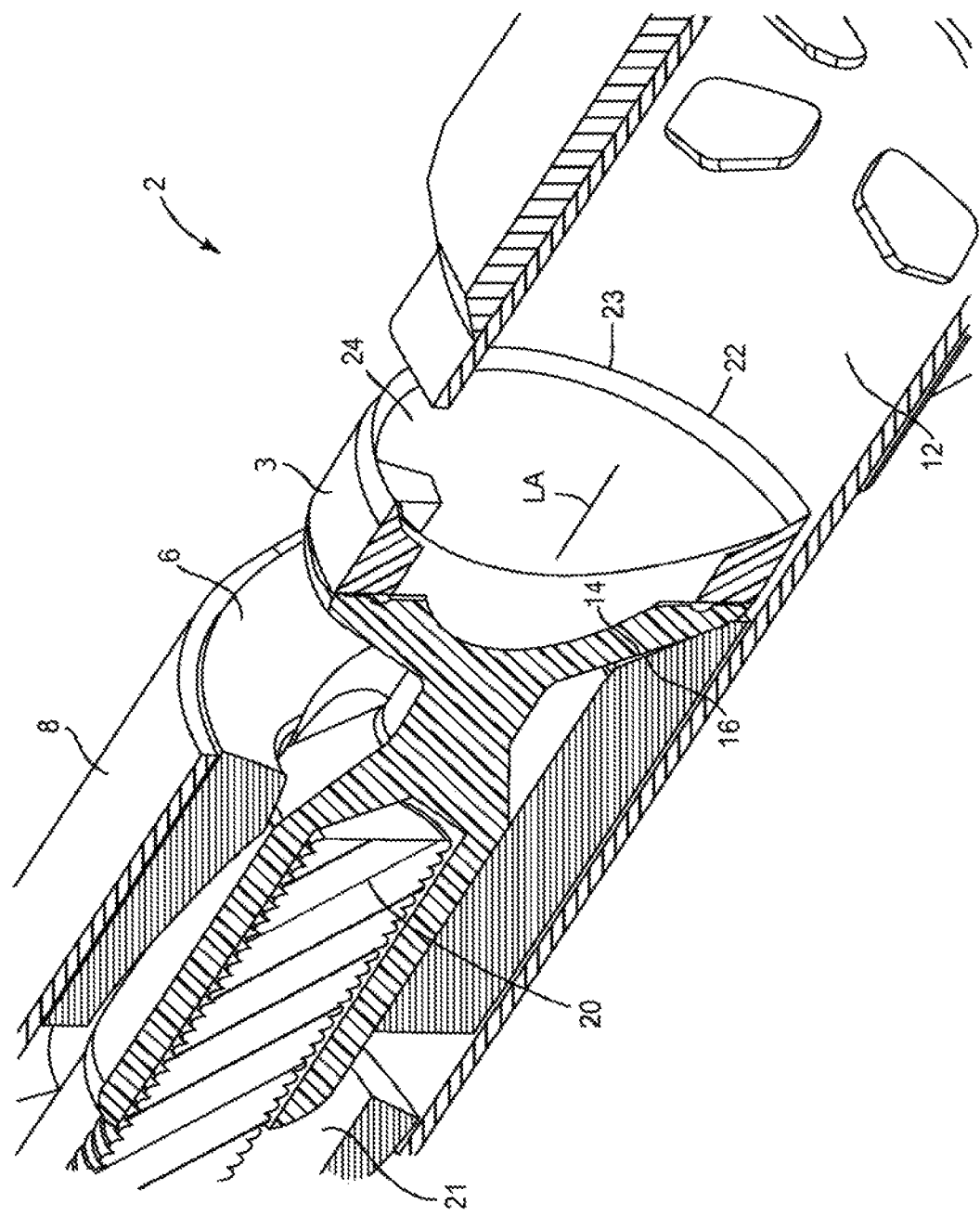
FIG. 2 is an enlarged fragmentary section of the atherectomy catheter of FIG. 1, illustrating one embodiment of a tissue-removing element in a stowed position.
Figure 3:
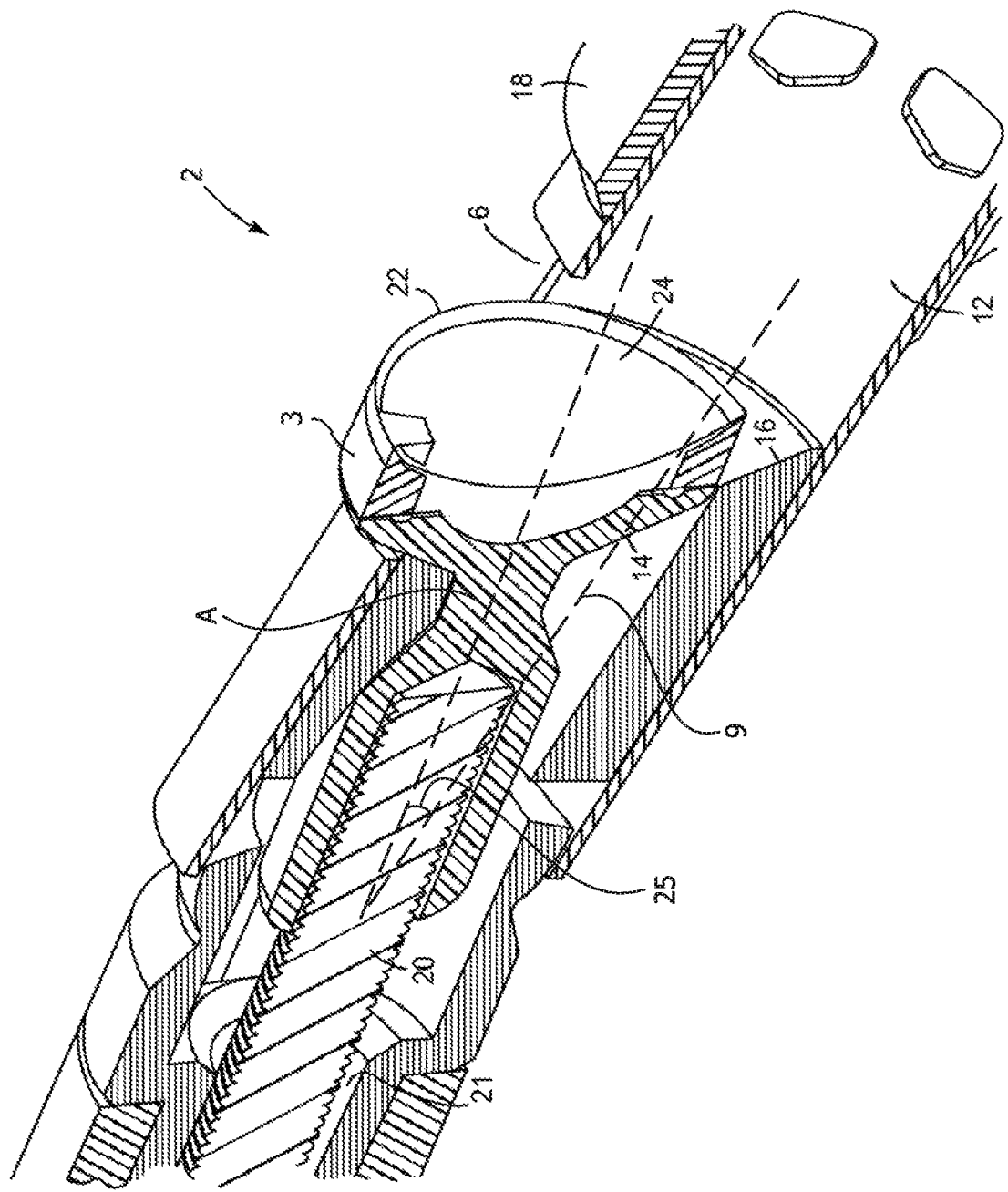
FIG. 3 is the enlarged fragmentary section of FIG. 1, illustrating the tissue-removing element in a deployed position.

Referring to FIGS. 1 to 3, an atherectomy catheter 2 (broadly, a "tissue-removing catheter"), which has a tissue-removing element 3 (broadly, a "tissue-removing element"), is used to cut material from a body lumen. The tissue-removing element 3 illustrated in FIGS. 1 to 3 is a conventional tissue-removing element. As will be explained below, tissue-removing element embodiments described in the present application are suitable replacements for the conventional tissue-removing element 3. That is, the tissue-removing element embodiments described herein below are suitable for use with the illustrated catheter 2 in place of the conventional tissue-removing element 3. The catheter 2 has an elongate body 8 having distal and proximal portions and sized and shaped for insertion into a body lumen of a subject. The tissue-removing element 3 is movable between a stored position (FIG. 2) and a cutting position (FIG. 3) relative to a window or opening 6 in the catheter body 8 adjacent the distal portion. The tissue-removing element 3 moves outwardly relative to the opening 6 so that an exposed portion of the element 3 extends outside the body 8 through the opening 6. The tissue-removing element 3 may be positioned relative to the body 8 and opening 6 so that less than 90 degrees of the tissue-removing element 3 is exposed to cut tissue. Of course, more of the tissue-removing element 3 may be exposed without departing from numerous aspects of the invention. Preferably, when the tissue-removing element 3 is in the cutting position, a longitudinal axis 28 of the tissue-removing element 3 is oriented at an attack angle 25 relative a longitudinal axis 9 of a leading portion of the catheter body 8.

Catheter 2 may have a maximum size of 3, 4, 5, 6, 7, 8, 9, 10, or 12 French (1, 1.3, 1.7, 2, 2.3, 2.7, 3, 3.3, or 4 mm) and may have a working length ranging of 20, 30, 40, 60, 80, 100, 120, 150, 180 or 210 cm depending on the requirements of the anatomical location in which use of the catheter is contemplated.

In the illustrated embodiment, the catheter 2 is moved distally through a vessel with the tissue-removing element 3 in the working or cutting position as described in further detail below. As the catheter 2 moves through the blood vessel, the tissue is cut by the tissue-removing element 3 and is directed into a tissue chamber 12 positioned distal to the tissue-removing element 3. The tissue chamber 12 may be somewhat elongate to accommodate the tissue that has been cut. It is understood that the catheter 2 may be configured to be moved proximally, rather than distally, within the body lumen in order to remove tissue. In such an embodiment, the tissue-removing element 3 would be oriented to face in the proximal direction, rather than the distal direction as illustrated. Accordingly, it is understood that the terms "distal" and "proximal" and the like used throughout the disclosure when referring to direction and relative locations of structures are not meant in a limiting sense, but are meant to apply to the embodiment as illustrated.

Referring to FIG. 3, the illustrated tissue-removing element 3 is moved proximally from the stored position so that a cam surface 14 on the tissue-removing element 4 engages a ramp 16 on the body 8 of the catheter 2. The interaction between the cam surface 14 and the ramp 16 causes the tissue-removing element 3 to move to the cutting position and also causes a tip 18 to deflect which tends to move the tissue-removing element 3 toward the tissue to be cut. The tissue-removing element 3 may be deployed in other ways without departing from the scope of the present invention.

The tissue-removing element 3 is coupled to a drive shaft 20 that extends through a lumen 21 in the catheter 2. The tissue-removing element 3 is rotated about an axis of rotation A in a rotational direction R when the drive shaft rotates about its longitudinal axis. The tissue-removing element 3 may be rotated at about 1 to 160,000 rpm in use but may be rotated at any other suitable speed depending upon the particular application. Other ways of driving rotation of the tissue-removing element 3 do not depart from the scope of the present invention.

Figure 4:
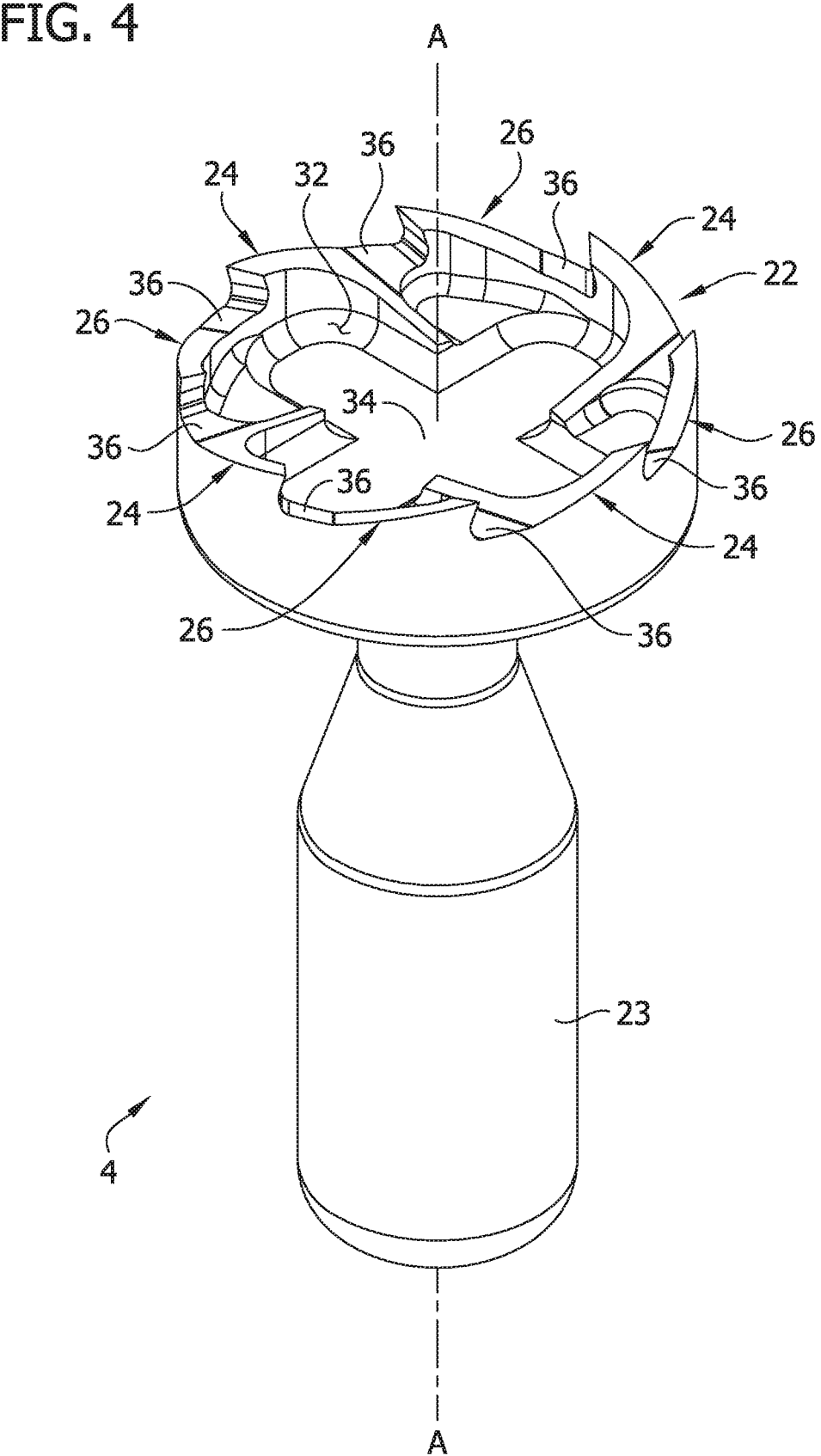
FIG. 4 is a perspective of the tissue-removing element.

Referring to FIG. 4, a first embodiment of a tissue-removing element of the present disclosure is generally indicated at reference numeral 4. The tissue-removing element has distal and proximal axial ends (broadly, "first and second axial ends"). The tissue-removing element 4 includes a tissue-removing head, generally indicated at reference numeral 22, at the distal axial end thereof. A stem 23 of the tissue-removing element 4 connects the tissue-removing element to the drive shaft 20. The tissue-removing head 22 comprises alternating primary and secondary tissue-removing components 24, 26, respectively, extending around the axis of rotation A. The primary tissue-removing components 24 are radially spaced from the axis of rotation A of the tissue-removing element 4 and angularly spaced from one another around the axis of rotation. Likewise, the secondary tissue-removing components 26 are radially spaced from the axis of rotation A and angularly spaced from one another around the axis of rotation. Each of the secondary tissue-removing components 26 is interposed between adjacent ones of the primary tissue-removing components 24. In the illustrated embodiment, the annular tissue-removing blade 22 comprises four primary tissue-removing components 24 and four secondary tissue-removing components 26 interleaved between the primary tissue-removing components. Though the illustrated embodiment uses four primary tissue-removing components 24 and four secondary tissue-removing components 26, it will be understood that any number of primary and secondary tissue-removing components can be used without departing from the scope of the invention. The primary and secondary tissue-removing components 24, 26 extend generally axially so that a radially central region of the tissue-removing element 4 at its distal end defines a recess 32 with a flat bottom surface 34. Gullets 36 are disposed between each adjacent primary tissue-removing component 24 and secondary tissue-removing component 26.

In the illustrated embodiment, the tissue-removing element 4 is integrally formed of one piece of material. Thus, the primary and secondary tissue-removing components 24, 26, respectively, are integrally formed of one piece of material. In other embodiments, it is contemplated that the tissue-removing element 4 can be a multi-piece assembly without departing from the scope of the invention. In one or more embodiments, the one-piece tissue-removing element 4 can be made from one of 465 stainless steel, 17-4 stainless steel, MP35N alloy, 35N LT alloy, titanium, and blends thereof. Other materials, such as other types of stainless steel, nickel, cobalt, chromium molybdenum, plastic, or combinations thereof, can also be used without departing from the scope of the invention.

Figure 5:
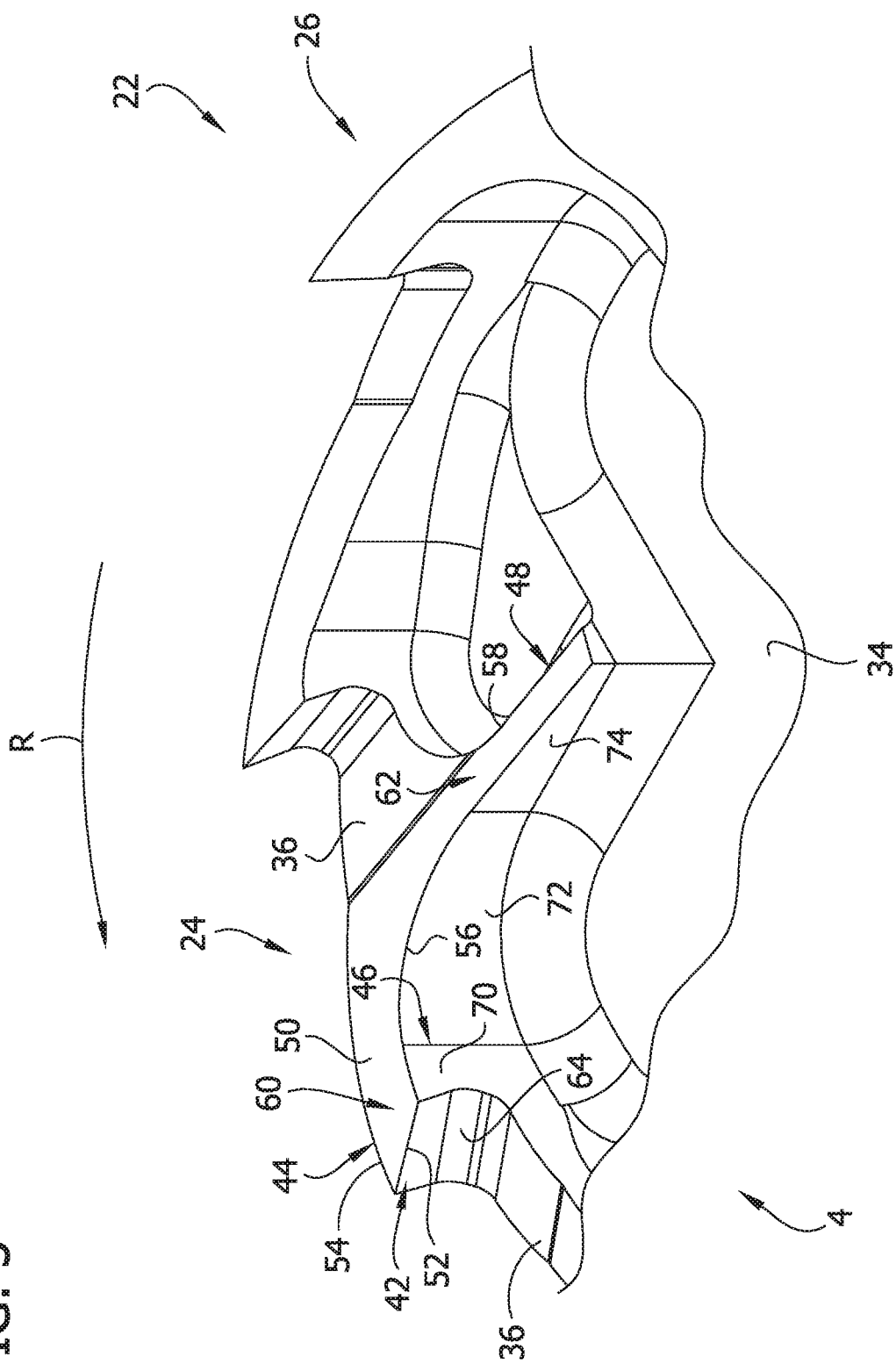
FIG. 5 is a fragmentary perspective of the tissue-removing element.

Referring to FIG. 5, each primary tissue-removing component 24 has a leading surface 42, a radially outer surface 44, a radially inner surface 46, and a trailing surface 48, each of which is indicated generally in the drawings and extends generally axially outward in the distal direction at the distal end of the tissue-removing element 4. The leading surface 42 is at the forward or leading end of the primary tissue-removing component 24 in the cutting direction R. An axial end surface 50 intersects each of the leading, radially outer, radially inner, and trailing surfaces 42, 44, 46, 48 at respective leading, radially outer, radially inner, and trailing edges 52, 54, 56, 58. The leading surface 42; the leading edge 52; and leading portions of the radially outer surface 44, the radially inner surface 46, the radially outer edge 54, and the radially inner edge 56 form a cutting tooth, generally indicated at 60. The trailing surface 48; the trailing edge 58; and trailing portions of the radially outer surface 44, the radially inner surface 46, the axial end surface 50, the radially outer edge 54, and the radially inner edge 56 form an inner shearing member (broadly, a raised element), generally indicated at 62.

Each integrally formed cutting tooth 60 and inner shearing member 62 operate together to engage hard and soft tissue in a body lumen and shear tissue (e.g., plaque) from the luminal wall, and bluntly impact the tissue so as to break the tissue free from the luminal wall. The integrally formed cutting tooth 60 and inner shearing member 62 operate together to effectively remove multiple types of tissue from a body lumen by attacking the tissue in multiple different ways as the tissue-removing element 4 advances axially through the body lumen and rotates in the cutting direction. As will be discussed in greater detail below, the integrally formed cutting tooth 60 and inner shearing member 62 are preferably formed by removing material from a blank with a cutting implement.

Referring to FIGS. 4 and 5, each secondary tissue-removing component 26 also defines a cutting tooth (indicated by the same reference number 26). However, the secondary tissue-removing components 26 do not define inner shearing members 62. As explained in more detail below, the parts of the secondary cutting teeth 26 are substantially similar to the corresponding parts of the primary cutting teeth 60, other than the absence of the integrally formed inner shearing members.

Figure 6:
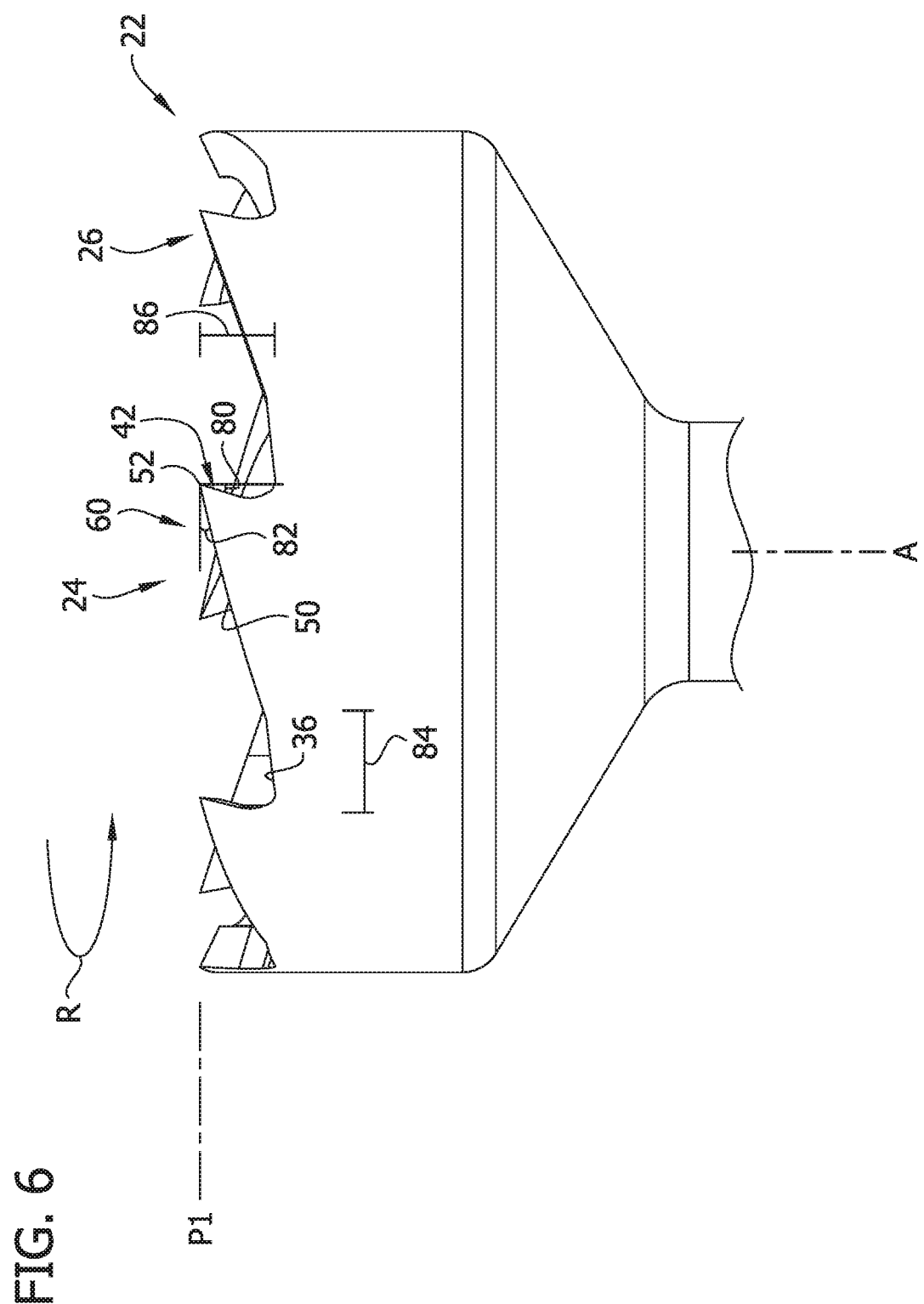
FIG. 6 is a fragmentary elevation of the tissue-removing element.

In the illustrated embodiment, as shown in FIG. 6, distal tips (e.g., the intersections of the leading edges 52 and the outer radially surfaces 44) of each of the primary and secondary cutting teeth 60, 26 define a cutting plane P1 oriented generally orthogonal to the axis of rotation A. Generally, the cutting plane P1 will be oriented generally orthogonal to the axis of rotation A of the tissue-removing element 4. However, it is contemplated that the cutting plane can be oriented at another angle with respect to the axis of rotation A without departing from the scope of the invention.

Reference is now made to one of the primary cutting teeth 60 with the understanding that the description set forth below applies equally to each of the primary cutting teeth. The primary cutting tooth 60 is adapted to cut tissue as the tissue-removing element 4 rotates to facilitate removal of soft tissue. Referring to FIG. 5, the leading surface 42 forming the primary cutting tooth 60 extends axially in the distal direction from the trailing end portion of the adjacent gullet 36 and radially between the radially outer surface 44 and radially inner surface 46. The leading surface 42 has an undercut 64 so that the leading edge 52 of the primary cutting tooth 60 is proud (i.e., leads in the cutting direction R) of at least a portion of the undercut. It will be understood that a cutting tooth may be formed without an undercut without departing from the scope of the invention. The leading portion 70 of the radially inner surface 46 forming the primary cutting tooth 60 is generally planar. The radially inner surface 46 extends axially in the distal direction from the flat bottom surface 34 of the recess 32 toward the radially inner edge 56. A distal portion of the radially inner surface 46 is oriented substantially perpendicular to the flat bottom surface 34 of the recess 32 and a proximal portion of the radially inner surface forms a radius between the distal portion thereof and the flat bottom surface.

Referring to FIG. 6, the leading surface 42 forming the primary cutting tooth 60 defines a rake angle 80 of the tooth. When viewed from a side-elevation as in FIG. 6, the rake angle 80 of the primary cutting tooth 60 is measured as the angle between the leading surface 42 relative to a line orthogonal to the cutting plane P1. Each cutting tooth 60 may have a positive rake angle 80 because the leading surface 42 of the cutting tooth trails the line perpendicular to the cutting plane P1 in the cutting direction R. The positive rake angle 80 of the primary cutting tooth 60 causes the leading surface 42 of the tooth to hook and pull soft tissue as it rotates in the cutting direction R. This strong engagement between the primary cutting tooth 60 and soft tissue helps the tissue-removing element 4 slice into soft tissue and pull it away from the body lumen wall. In addition, due to the positive rake angle 80, when the primary cutting tooth 60 engages hard tissue as it rotates in the cutting direction R, it imparts a high degree of stress on the tissue because the force imparted on the tissue is concentrated at the leading edge 52 forming the tooth. In one or more embodiments, the rake angle 80 of the primary cutting tooth 60 may be from about +5° to about +35°. However, it will be understood that other rake angles can also be used without departing from the scope of the invention. For example, in certain embodiments, the cutting teeth have negative rake angles.

Referring still to FIG. 6, in the illustrated embodiment, the primary cutting tooth 60 has a relief angle 82, which is the angle between the cutting plane P1 and the portion of the axial end surface 50 defining the cutting tooth. In one or more embodiments, the tooth relief angle 82 is chosen to maximize a width 84 of the gullet 36 without compromising the robustness of the primary cutting tooth 60 or the operation of the catheter 2. An excessively large relief angle 82 may remove too much material from the leading portion of the primary cutting tooth 60, which may weaken the structure thereof. In addition, an excessively large relief angle 82 may cause the primary cutting tooth 60 to engage tissue at a depth which requires the drive shaft 20 to produce a large amount of torque to effectively remove the tissue. This may cause the catheter 2 to fail (e.g., a broken driveshaft, stalled motor, etc.) or the cutting tooth 60 to disengage from the tissue rather than break through it as the tissue-removing element 4 rotates in the cutting direction R. If the relief angle for the cutting tooth 60 is too small, the tissue-removing element 9 will not advance axially through tissue in the lumen at the desired rate. When the tissue-removing element 4 is formed by removing material from a generally cylindrical blank (as explained below), a larger gullet width 84 (such as shown in FIG. 6) allows large cutting implements to be passed over the gullet and used to cut away material of the blank inside the recess 32. In one or more examples, the relief angle 82 may be about 14°. However, it will be understood that other relief angles can also be used without departing from the scope of the invention.

As shown in FIG. 6, a tooth height 86 of the primary cutting tooth 60 is the dimension in the axial direction between the distal tip of the primary cutting tooth and the proximal-most point of the cutting tooth, where it begins to extend in the axially distal direction away from the adjacent, leading gullet 36. In the illustrated embodiment, the tooth height 86 may be about 0.005 inches; however, other tooth heights can also be used without departing from the scope of the invention.

Figure 7:
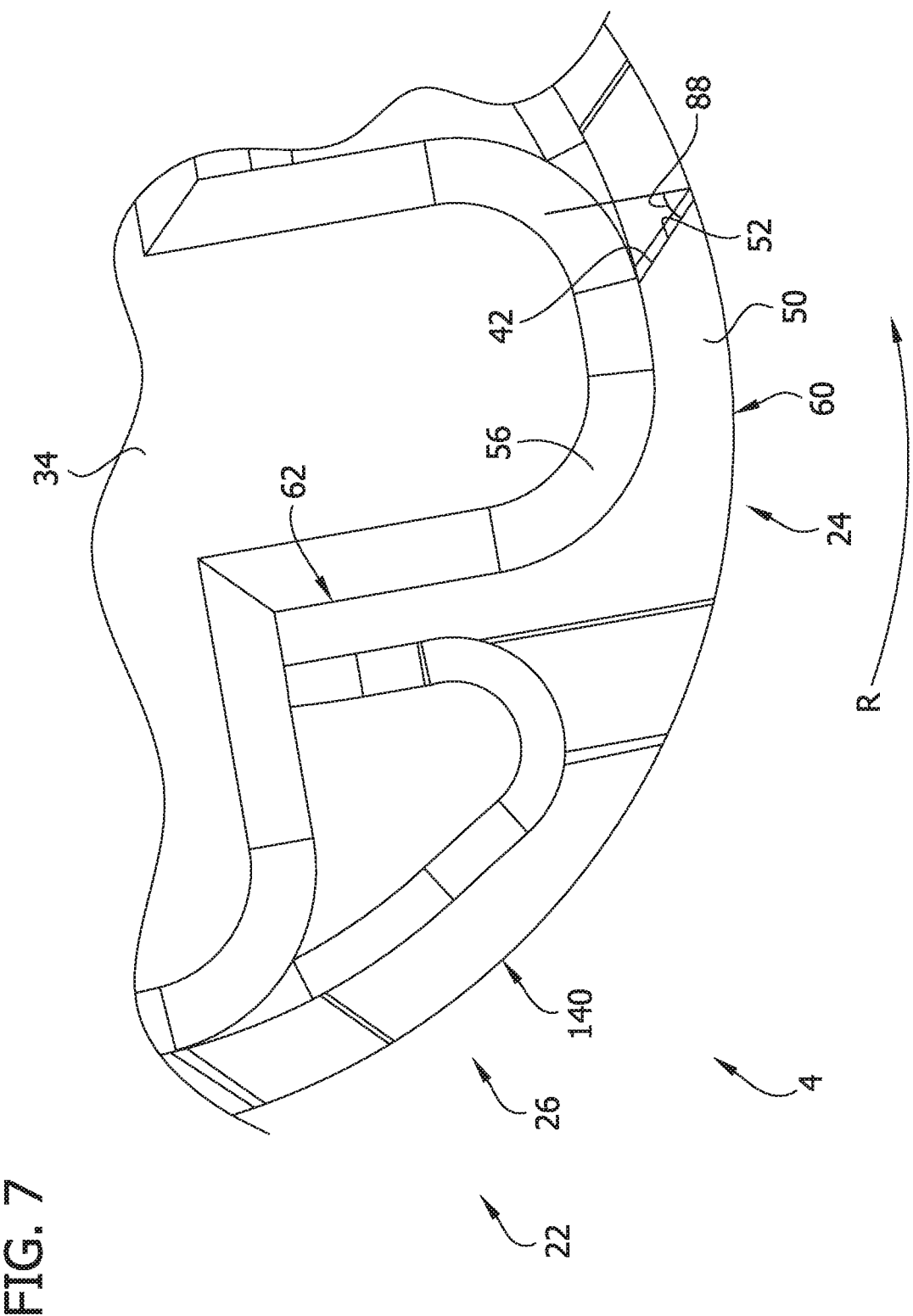
FIG. 7 is a fragmentary top plan view of the tissue-removing element.

Referring to FIG. 7, the leading edge 52 forming the primary tooth 60 defines a fleam angle 88 of the cutting tooth 60. When the tissue-removing element 4 is viewed from the distal axial end as shown in FIG. 7, the fleam angle 88 of the primary cutting tooth 60 is the angle between the leading edge 52 and a line perpendicular to a line tangent to the perimeter of the annular tissue-removing head 22. A greater fleam angle 88 creates a sharper cutting tooth 60 that slices through soft and hard tissue more efficiently. In addition, when the fleam angle 88 is greater than 0°, the leading surface 42 of a cutting tooth 60 engages tissue at an angle, which causes the tissue to shear radially inwardly. By comparison, the leading surface of a cutting tooth with a fleam angle of 0° (not shown) engages tissue at a substantially normal angle relative the linear direction of its motion, which may not cause shearing. The improved tissue-removing properties of the primary cutting tooth 60 with a non-zero fleam angle 88 are balanced against the robustness of the leading portion of the cutting tooth. A larger fleam angle 88 results in less material at the leading portion of the primary cutting tooth 60, which may adversely affect robustness. In one or more embodiments the fleam angle 88 is greater than 0°, such as from about 1° to about 60°.

Figure 8:
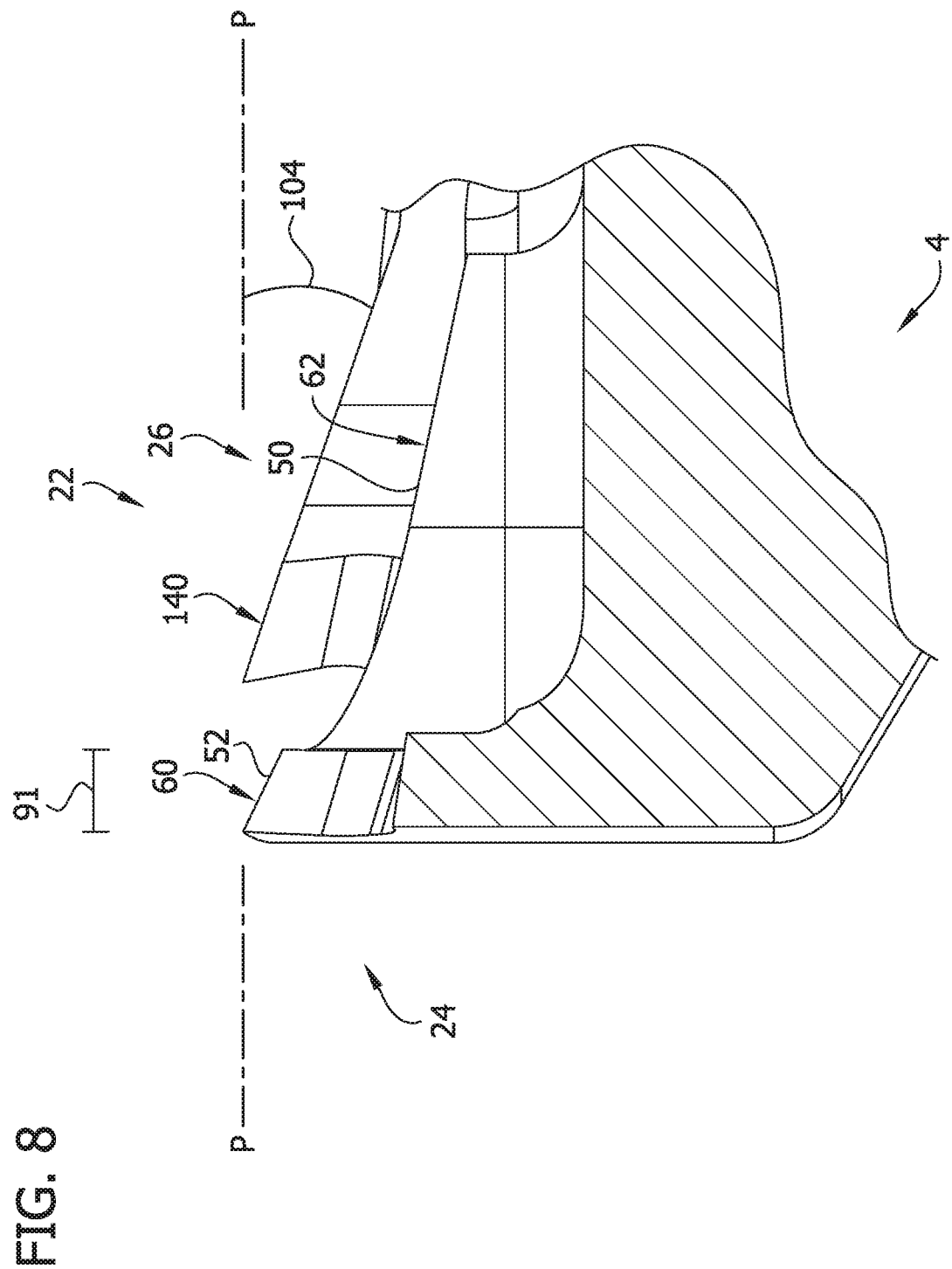
FIG. 8 is fragmentary section of the tissue-removing element.

As shown in FIG. 8, the primary cutting tooth 60 has a tooth thickness 91 measured in the radial direction between the radially inner and outer surfaces 46, 44. When the cutting tooth 60 cuts through hard tissue, it makes a kerf in the tissue having a width that substantially corresponds to the tooth thickness 91. When the cutting tooth 60 cuts through soft tissue, it cleaves, slices, or shears the tissue, creating a crevice or other deformation that substantially corresponds in thickness with the tooth thickness 91. The tooth thickness 91 affects the robustness of the cutting tooth 60 and its engagement with hard and soft tissue. A greater tooth thickness 91 improves robustness because the primary cutting tooth 60 comprises more material, which enhances strength. However, a lesser tooth thickness 91 allows the cutting tooth 60 to pass with less resistance through tissue as it rotates in the cutting direction R. In one or more embodiments, the thickness 91 of the primary cutting tooth 60 is substantially constant along its height 86 and may measure from about 0.0005 inches to about 0.0100 inches, and in one embodiment, about 0.0035 inches. In one or more embodiments, the thickness 91 of each cutting tooth 60 may be from about 1% to about 50% of the outer radius of the tissue-removing head 22. Other tooth thicknesses can also be used without departing from the scope of the invention. In the illustrated embodiment, the thickness of the portion of the cutting head 22 that trails the inner shearing member 62 is thicker than the thickness 91 of the cutting tooth 60 so that a large cutting implement can be used to form the radially inner surfaces of the trailing primary and secondary tissue-removing components 24, 26.

In the illustrated embodiment, a section taken along the height 86 of the primary cutting tooth 60 has a generally trapezoidal shape with sides that are generally parallel. In other embodiments, a section taken along the height 86 of the primary cutting tooth 60 may have a generally wedge shape. A cutting tooth with a wedge sectional shape has sides that are oriented at an angle relative to one another such that the cutting tooth is narrower at one axial end than the other axial end. A wedge sectional shape tends to cause tissue to bend radially inward toward the axis of rotation A of the tissue-removing element 4 as the catheter 2 is advanced in the axial direction and the tissue-removing element rotates about its axis of rotation A. By comparison, the illustrated cutting tooth 60, with its trapezoidal sectional shape, tends to bite through hard tissue rather than bend the tissue. It is contemplated that a tissue-removing element could also have a wedge sectional shape or other sectional shape without departing from the scope of the invention.

The construction of the exemplary inner shearing members 62 will now be described. Generally, each of the shearing members 62 functions to aid the cutting teeth 60, 26 in removing tissue from a body lumen. Reference is now made to one of the inner shearing members 62, with the understanding that the description set forth below applies equally to each of the inner shearing members. Referring to FIG. 5, the inner shearing member 62 is adapted to impact tissue and shear it radially inwardly as the tissue-removing element 4 rotates to facilitate removal of hard tissue. The radially inner surface 46 has an arcuate portion 72 that curves radially inward relative to the axis of rotation A, away from the radially outer surface 44 and toward a trailing portion 74 of the radially inner surface, forming the inner shearing member 62. The trailing portion 74 of the radially inner surface 46 extends radially inward relative to the axis of rotation A in a direction generally transverse to the perimeter of the annular tissue-removing head 22. The axial end surface 50 and the arcuate and trailing portions 72, 74 (along with the trailing surface 48) form the inner shearing member 62. The axial end surface 50 forming the inner shearing member 62 is substantially planar and lies in a different plane than the trailing, adjacent gullet 36. Thus, the axial end surface 50 forms an angle less than 180° relative the gullet 36.

In the illustrated embodiment, the arcuate portion 72 of the radially inner surface 46 of each primary tissue-removing component 24 is configured to shear tissue radially inward with respect to the tissue-removing element 4. The trailing portion 74, which acts as the impact surface of the inner shearing member 62, is configured to impact tissue at an obtuse angle to further shear the tissue radially inwardly as the tissue-removing element 4 rotates in the cutting direction R. The arcuate portion 72 has a radius of curvature 92, and the trailing portion 74 has a length 94 (See FIG. 9). The dimensions for the radius of curvature 92 and the length 94 affect the shearing action of the arcuate portion 72 and the impacting action of the trailing portion 74 and are limited by the available space for the inner shearing member 62. In the illustrated embodiment, the radius of curvature 92 may be about 0.0085 in. In one or more embodiments, the radius of curvature 92 of the arcuate portion 72 of the inner shearing member 62 may be from about 1% to about 50% of the radius of the outer tissue-removing blade 22. Likewise, in one or more embodiments, the length 94 of the impact surface of an inner shearing member (e.g., the trailing portion 74 of the radially inner surface 46) may be from about 1% to about 75% of the radius of the outer tissue-removing blade 22.

Figure 9:
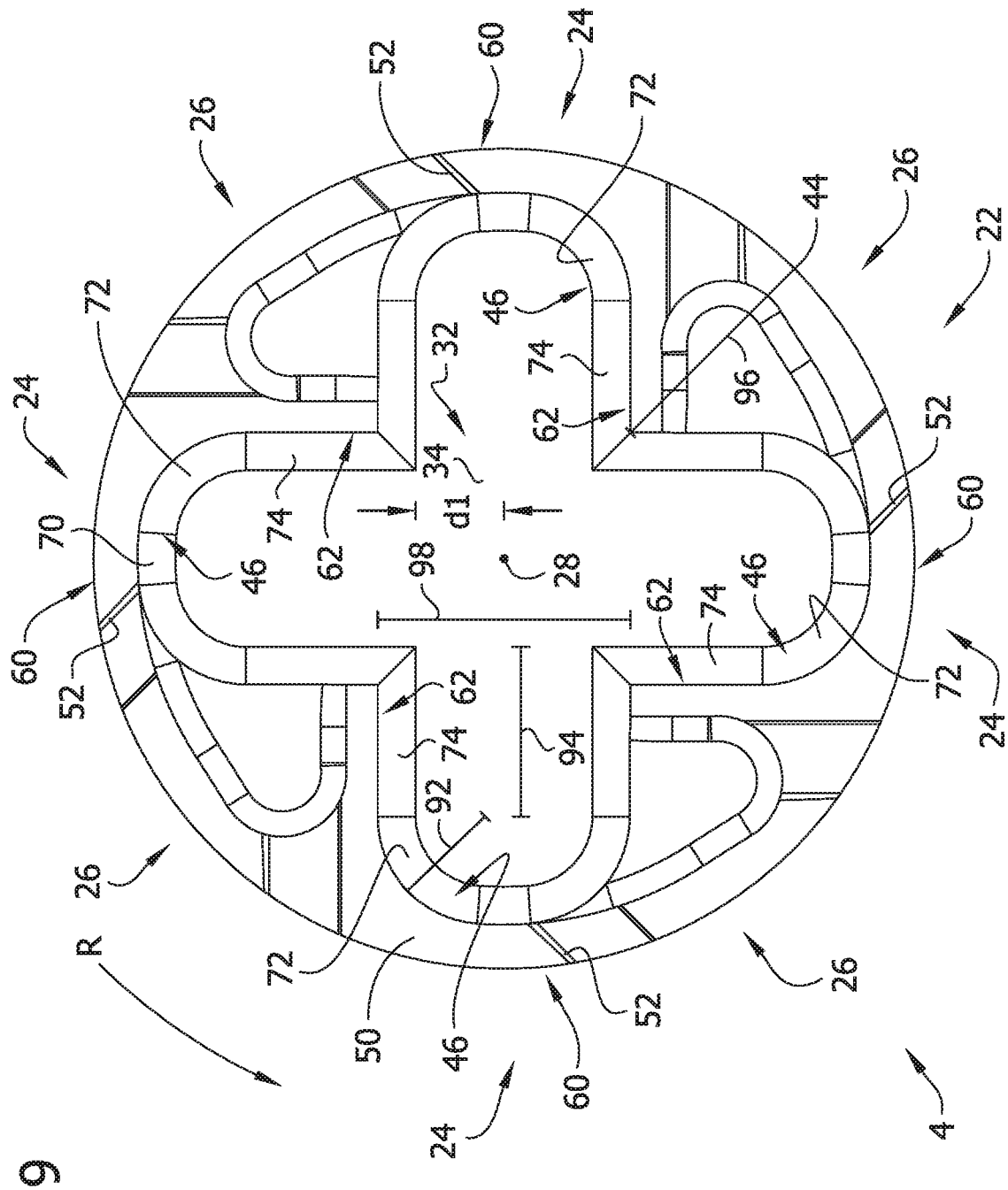
FIG. 9 is a top plan view of the tissue-removing element.

Referring to FIG. 9, in the illustrated embodiment, the four inner shearing members 62 are formed in a crosscut pattern (i.e., the flat bottom surface 34 of the recess 32 is cross-shaped). The crosscut pattern enables the inner shearing members 62 to be machined relatively easily using a single cutting implement at a fixed axial cutting depth. A crosscut width 98 measures the distance between the trailing end of one inner shearing member 62 and the impact surface (i.e., the trailing portion 74 of the radially inner surface 46) of the adjacent, trailing inner shearing member. The crosscut width 98 is preferably chosen to optimize the angle of impact of the inner shearing member 62. When the impact surface 74 is in line with a radius of the tissue-removing head 22, the inner shearing member impacts hard tissue at an impact angle perpendicular to the impact surface, which causes braking of the rotation of the tissue-removing element 4 and reduces tissue-removal efficiency. In the illustrated embodiment, the plane of the impact surface 74 of each inner shearing member 62 is offset a distance d1 (e.g., about 0.010 inches) from the axis of rotation A in a direction perpendicular to the plane. As a result, the impact surface 74 of each inner shearing member 62 impacts hard tissue at an obtuse impact angle. This reduces the tendency of impacts between one of the inner shearing members 62 and hard tissue to cause braking of the rotation of tissue-removing element 4. In addition, it enables impacts between the tissue and the impact surface 74 to shear the tissue away from the body lumen wall. As compared with a purely blunt impact that does not tend to shear the tissue, the shearing caused by the impact surface is believed to improve the efficiency with which the tissue-removing element 4 fractures hard tissue.

Referring still to FIG. 9, each inner shearing member 62 has a radial length 96 that is measured as the distance between the radially outer surface 44 of the tissue-removing head 22 and the radially innermost point of the inner shearing member 62 along an imaginary line that passes through both the axis of rotation A and the innermost point of the inner shearing member 62 in a plane parallel to the cutting plane P1. To maximize the capability of the inner shearing member 62 to impact tissue at any radial position in the body lumen, the radial length 96 may be equal to the radius of the tissue-removing head 22. However, to facilitate the crosscut pattern by which the inner shearing members 62 are manufactured, the inner shearing member radial length 96 is preferably less than the radius of the tissue-removing head 22. In one or more embodiments, the inner shearing member radial length 96 may be from about 10% to about 80% of the radius of the tissue-removing head 22. In the illustrated embodiment, the inner shearing member radial length 96 may be about 0.018 in. In one or more embodiments, the breaker radial length 96 is sized so that, as the cutting element 4 rotates in the deployed position, the primary tissue-removing component 24 spans the entire distance between the cutter opening 6 and the wall of the body lumen. This arrangement maximizes the engagement between the inner sharing member 62 and the tissue. Alternatively, the breaker radial length 96 can be sized so that, as the cutting element 4 rotates in the deployed position, the primary tissue-removing component 24 spans only a radially outer portion of the distance between the cutter opening 6 and the wall of the body lumen. This arrangement allows the flat surface 34 of the recessed portion of the cutting head 22 to redirect cut tissue toward the tissue chamber 12.

Figure 10:
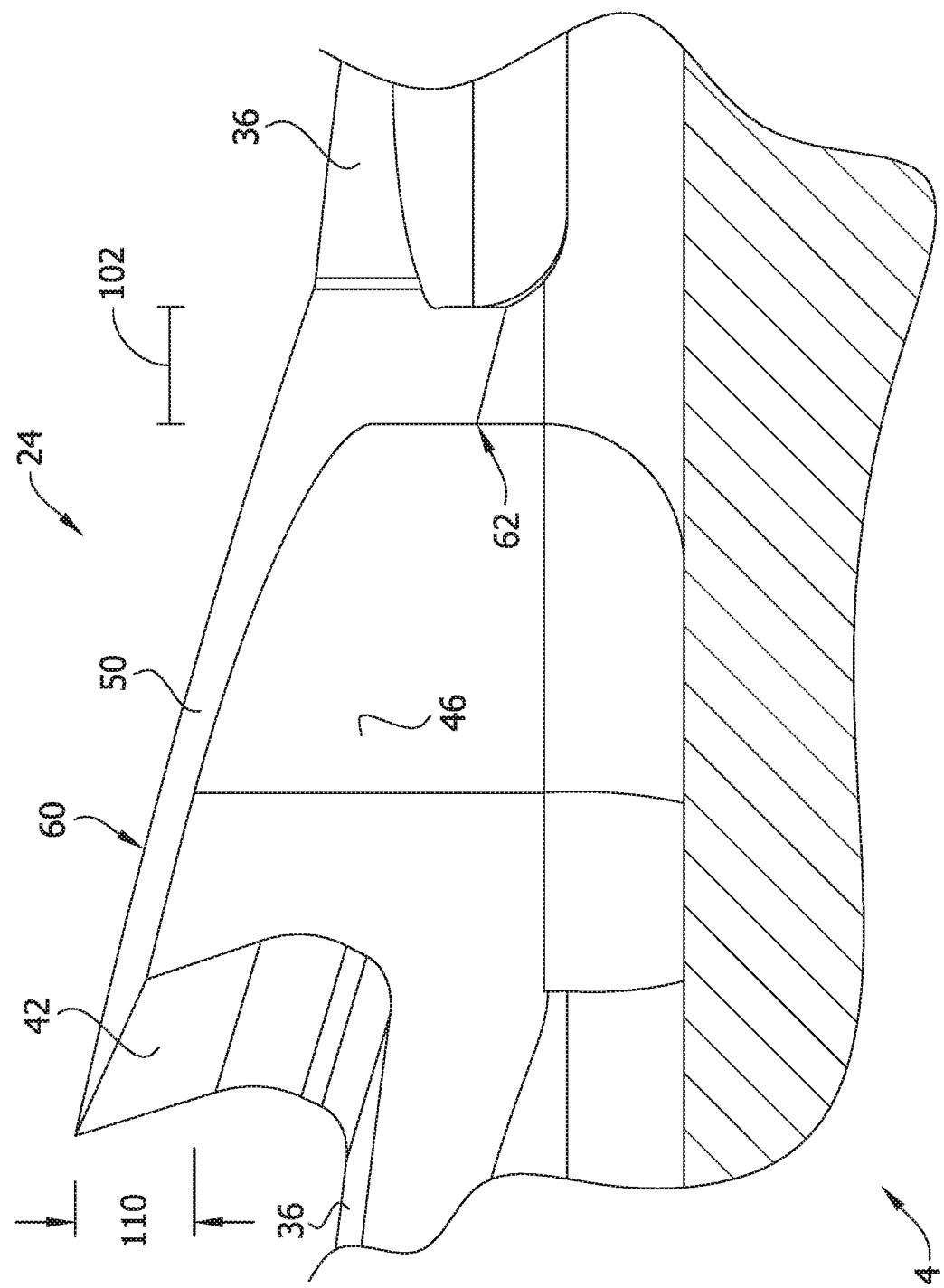
FIG. 10 is another fragmentary section of the tissue-removing element.

As shown in FIG. 10, the inner shearing member 62 has an inner shearing member thickness 102. The inner shearing member thickness 102 affects the gullet width 84 (FIG. 6) and the robustness of the inner shearing member 62. The inner shearing member thickness 102 also affects the size of cutting implement used to form the radially inner surfaces of the trailing primary and secondary cutting elements 24, 26. The gullet width 84 is preferably sufficiently small so that the planar axial end surface 50 can extend continuously from the cutting tooth 60 through the entire thickness 102 of the inner shearing member 62. In the illustrated embodiment, the inner shearing member thickness 102 may be about 0.0025 in or about 8% of the outer radius of the tissue-removing element 4. In one or more embodiments, the inner shearing member thickness may be from about 1% to about 30% of the outer radius of the tissue-removing element 4. In other embodiments, the inner shearing member thickness 102 can be other dimensions without departing from the scope of the invention.

Figure 11:
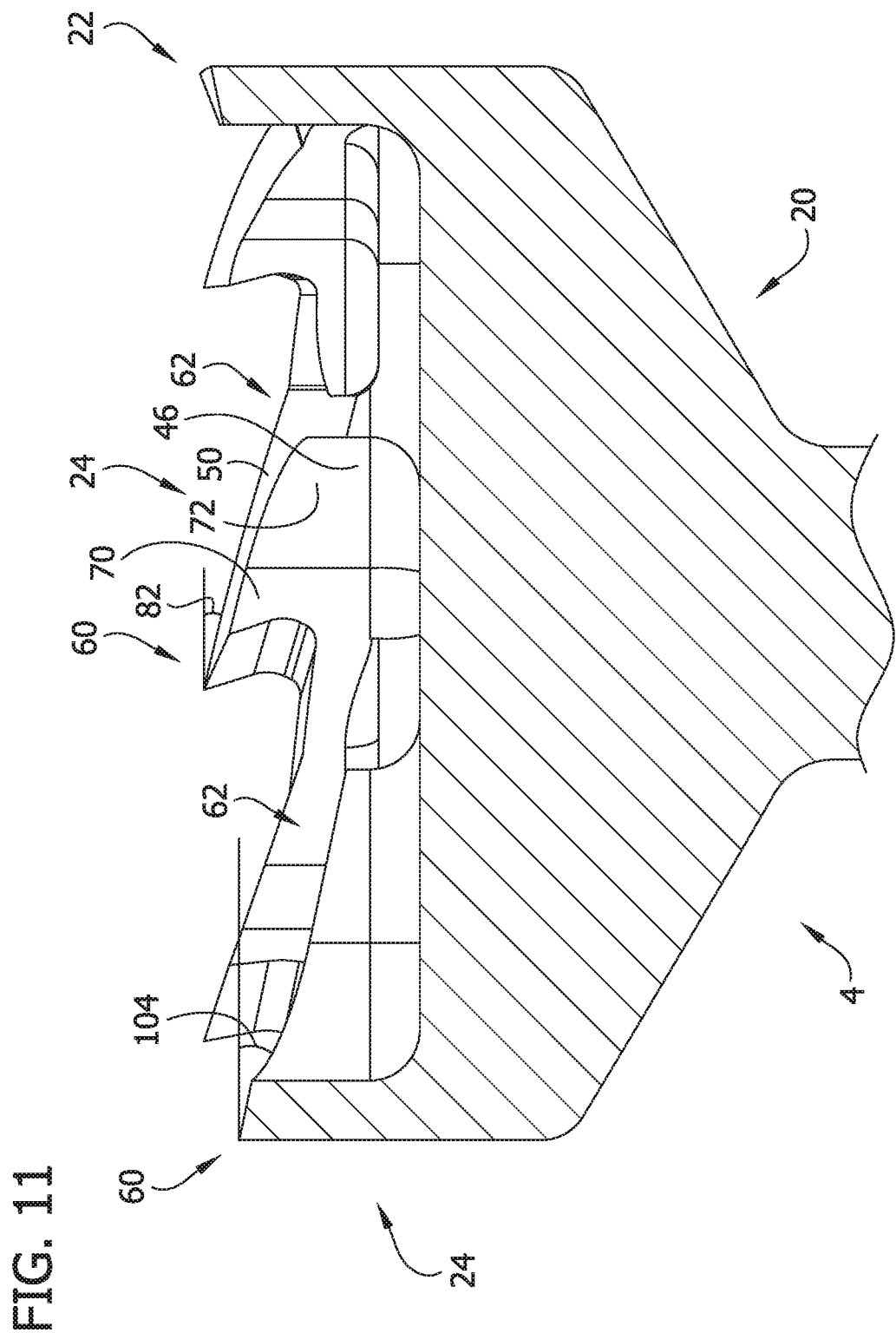
FIG. 11 is another fragmentary section of the tissue-removing element.

Referring to FIGS. 8 and 11, the axial end surface 50 of each primary tissue-removing component 24 is a continuous planar surface that spans the cutting tooth 60 and the inner shearing member 62. The axial end 50 and the leading edge 52 of the cutting tooth 60 may be tilted or sloped inward from the radially outer surface 44 to the radially inner surface 46 relative to the cutting plane P1 at a tilt angle 104. Thus, the axial end surface 50 is oriented at the relief angle 82 and the tilt angle 104. For each primary tissue-removing component 24, the axial end surface 50 of the cutting tooth 60 and the inner shearing member 62 can be formed together by selectively orienting a cutting implement at a desired angle relative the axis of rotation A of the tissue-removing element 4 and removing material therefrom with the cutting implement oriented at the desired angle, without changing the angle of the cutting implement relative the axis of rotation.

Since the axial end surface 50 is a continuous planar surface that spans the cutting tooth 60 and the inner shearing member 62, the axial end surface of the inner shearing member 62 is oriented at the tilt angle 104 with respect to the cutting plane P1. As discussed above, the tissue-removing element 4 extends through the tissue-removing element window 6 of the catheter 2 at an attack angle 25 relative the longitudinal axis of the distal portion of the catheter body 8 (See FIG. 3). Preferably, the tilt angle 104 of the axial end surface 50 of each inner shearing member 62 is operable to permit the inner shearing member to engage tissue. If the tilt angle 104 is too low, engagement between the inner shearing member 62 and tissue can cause the tissue-removing element 4 to move away from the tissue as the catheter 2 advances in the axial direction. However, if the tilt angle 104 of the inner shearing member 62 is too high, the inner shearing member of the cutting element 4 can advance toward the tissue in the body lumen with such high force that excessive friction between the tissue and the cutting element is created. Preferably the tilt angle 104 is chosen to inhibit the tissue-removing element 4 from moving away from the tissue and to likewise inhibit the tissue-removing element from advancing toward the tissue with such high force as to create excessive friction between the tissue-removing element and the tissue. In preferred embodiments, the tilt angle is greater than or equal to the attack angle 25.

As shown in FIG. 10, each of the primary tissue-removing components 24 has an inner shearing member depth 110 measured as the axial distance between the distal-most end of the cutting tooth 60 and the distal-most end of the inner shearing member 62. In the illustrated embodiment, the distal-most end of the cutting tooth 60 is the distal tip of the primary tissue-removing component 24 at the radially outer surface 44. The distal-most end of the inner shearing member 62 is the distal end (and leading end) of the arcuate portion 72 of the radially inner surface 46. Because the trapezoidal shaped cutting tooth 60 bites through hard tissue in the body lumen rather than bending the tissue radially inward toward the axis of rotation A, an inner shearing member depth 110 greater than zero does not hinder the cutting efficiency of the primary tissue-removing components 24. By comparison, when a wedge-shaped kerf causes tissue to bend radially inward, the bent tissue increases the friction on the tissue-removing element as it rotates and pushes back against the axial advancement of the catheter 2 through the body lumen, thereby hindering cutting efficiency. As a result, to maximize cutting efficiency, it is preferable to minimize the inner shearing member depth 110 with a cutting tooth that has a wedge-shaped cross-sectional shape. However, due to other design factors and manufacturability considerations, it can be preferable to have a larger inner shearing member depth 110. In the illustrated embodiment, the inner shearing member depth 110 may be about 0.0023 in. Other inner shearing member depths can also be used without departing from the scope of the invention.

A minimum tooth height 111 also affects cutter efficiency and engagement. In the illustrated embodiment, the minimum tooth height 111 is measured as the axial distance between the distal tip of the radially inner surface 46 forming the cutting tooth 60 and the distal-most end of the inner shearing member 62. For cutting teeth that create a kerf in hard tissue like the cutting tooth 60, the maximum tooth height 111 is believed to affect the ability of the cutting head 22 to stay engaged in tissue as it rotates in the body lumen. If the minimum tooth height 111 is too small, the tooth 60 will create a shallow kerf in the tissue, and the trailing cutting teeth 26, 60 will have difficulty remaining radially aligned with the kerf. If the minimum tooth height is too great, the cutting tooth 60 will engage too deeply in the tissue, which can hinder operation of the catheter as discussed above.

Figure 12:
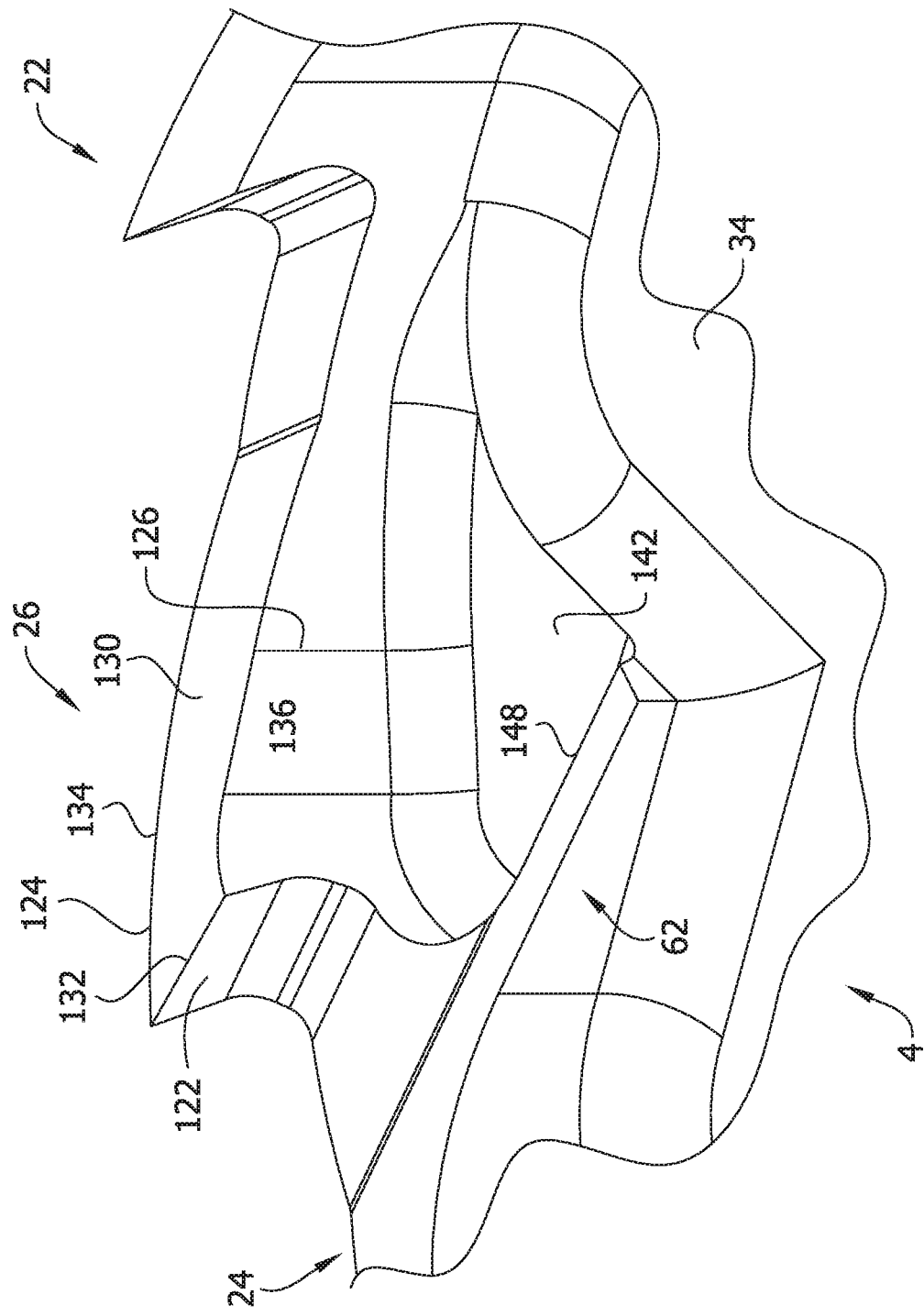
FIG. 12 is another fragmentary perspective of the tissue-removing element.

Referring to FIG. 12, each of the secondary tissue-removing components 26 (defining the secondary cutting teeth indicated by the same reference numeral 26) has a leading surface 122, a radially outer surface 124, and a radially inner surface 126 extending generally axially. In use, the leading surface 122 is at the forward end of the secondary tissue-removing component 26 as the tissue-removing element 4 rotates in the cutting direction R. An axial end surface 130 intersects each of the leading, radially outer, and radially inner surfaces 122, 124, 126 at respective leading, radially outer, and radially inner edges, 132, 134, 136. The leading, radially outer, radially inner, and axial end surfaces 122, 124, 126, 130 and leading, radially outer, and radially inner edges 132, 134, 134 define the secondary cutting tooth 26. An axially raised portion 142 extends axially in the distal direction between the trailing surface 148 of a primary tissue-removing component 24 and an adjacent, trailing secondary tissue-removing component 26. The raised portion 142 provides additional support and strength for the inner shearing member 62 of the primary tissue-removing component 124. However, being spaced apart proximally from the trailing edge 48 of the inner shearing member, the raised portion 142 also provides relief for tissue passing over the inner shearing member. The shallower depth of the raised portion 142 relative the flat surface 34 enables the radially inner surface of the gullet 36 to be machined more efficiently.

In the illustrated embodiment, the secondary cutting teeth 26 have rake angles, relief angles, tooth heights, fleam angles, and cross-sectional shapes that generally match those of the primary cutting teeth 60. As a result the same cutting implement(s) used to form the primary cutting teeth 60 can also be used to form the secondary cutting teeth 26. The secondary cutting teeth 60 improve the engagement of the cutting element 4 by increasing the surface area that is contacting the tissue at any given time (e.g., rather than a single primary tissue-removing component contacting the tissue, a primary tissue-removing component and portions of one or more secondary tissue-removing components might contact the tissue at the same time). In addition, the secondary cutting teeth 26 engage tissue in a body lumen in the same way as the primary cutting teeth 60 as the catheter 2 advances axially therein and the tissue-removing element 4 rotates in the cutting direction R. Although the illustrated secondary cutting teeth 26 have substantially the same geometry as the primary cutting teeth 60, the rake angle, relief angle, tooth height, fleam angle, and/or cross-section shape of the secondary cutting teeth could also be different than the primary cutting teeth without departing from the scope of the invention.

In an exemplary method of making the tissue-removing element 4, the tissue-removing element can be formed by removing material from a blank comprising a single piece of material using one or more cutting implements. In one or more embodiments, a blank comprises a generally cylindrical body of material with opposite first and second axial ends and an axis extending between the axial ends. In certain embodiments, only an axial end portion at the first axial end of the blank, which corresponds with the distal end of the tissue-removing element 4, is cylindrical. Thus, the blank can be preformed to have the shape of the proximal end portion of the tissue-removing element 4 or can be machined to form the shape of the proximal end portion of the tissue-removing element 4 as part of a method of making a tissue-removing element without departing from the scope of the invention.

In one method of making a tissue-removing element, a cutting implement, such as a milling cutter of a multi-axis mill or Swiss machine, removes material from the blank to form the primary cutting teeth 60 of the primary tissue-removing components 24 and likewise removes material from the blank to form the inner shearing member 62 of the primary tissue-removing components. For each primary tissue-removing component 24, the cutting implement preferably forms portions of the primary cutting tooth 60 and inner shearing member 62 simultaneously (i.e., in the course of a single pass of the cutting implement along a cutting path). A cutting implement preferably removes material from the blank to form a leading surface 42, radially inner surface 46, and contiguous axial end surface 50 to form one of the primary cutting teeth 60 and the corresponding inner shearing member 62. A cutting implement also removes material from the blank to form the gullets 36, the secondary tissue-removing components 26, and the recess 32.

In one or more embodiments, a single cutting implement is used to form the radially inner surface 46 forming the cutting tooth 60 and inner shearing member 62 of each primary tissue-removing component 24. For example, the radially inner surface 42 of the cutting tooth 60 and the inner shearing member 62 of each primary tissue-removing component 24—including the leading portion 70, the arcuate portion 72, and the trailing portion 74 of the radially inner surface—is formed in a single, continuous pass of the cutting implement along a cutting path oriented parallel to the axially extending surface portion of the radially inner surface 46. This single continuous pass of the cutting implement can, for example, comprise a finishing pass of the cutting implement after the bulk of the blank material adjacent the radially inner surface 46 has already been removed, or it can comprise an initial pass of the cutting implement before the radially inner surface has been otherwise formed. Likewise, in one or more embodiments, the flat bottom surface 34 of the recess 32 is formed using the same cutting implement as is used to form the radially inner surfaces 46 of the primary tissue-removing components 24.

In certain embodiments, a cutting implement oriented at a selected angle relative the axis of rotation A and cutting plane P removes material from the blank to form the axial end surface 50 of each cutting tooth 60 and inner shearing member 62 of a corresponding primary tissue-removing component 24. The selected angle of the cutting implement is chosen so a material-removal plane thereof is co-located with the axial end surface 50 of the cutting tooth 60. Preferably, the cutting implement performs one or more operations (i.e., passes of the cutting implement along a cutting path) with the cutting implement oriented at the selected angle relative the axis of rotation A and cutting plane P. The orientation of the cutting implement at the selected angle does not change for forming the axial end surface 50 of the cutting tooth 60 or inner shearing member 62. In certain embodiments, after the axial end surface 50 of one of the primary tissue-removing components 24 is formed, the blank is rotated a quarter-turn about its longitudinal axis and the cutting implement performs the same operations to remove material from the blank to form the axial end surface of an adjacent primary tissue-removing component. Additionally or in the alternative, the blank can be rotated one-eighth of one turn to form the axial end surface 130 of the secondary cutting tooth 26, which in the illustrated embodiment has the same relief angle and tilt angle as the primary tissue-removing component 24. The steps of rotating the blank and using the cutting implement in the selected orientation to perform the same operations is repeated two more times until the axial end surfaces 50, 130 of each of the primary tissue-removing components 24 and, optionally, the secondary tissue-removing components 26 are formed.

In an exemplary method of using the catheter 2 to remove tissue from a body lumen will now be described. A user inserts the catheter 2 into the body lumen (such as by using a guidewire), positions the tissue-removing element 4 in the deployed position, and rotates the tissue-removing element in the cutting direction R as the catheter advances axially through the lumen. Each primary tissue-removing element 24 engages and removes tissue (e.g., plaque) from the body lumen as it rotates about its rotation axis A and advances axially through the lumen. With respect to one of the primary tissue-removing components, the primary cutting tooth 60 of one of the primary tissue-removing components 24 engages the tissue first, before the corresponding inner shearing member 62, since it is the leading portion of the primary tissue-removing component. As the tissue-removing element 4 rotates in the cutting direction R, the leading surface 42 engages the tissue and shears it radially inward, toward the axis of rotation A. As the catheter 2 advances axially (e.g., distally) in the body lumen, the cutting tooth 60 bites through hard tissue, removing some of the tissue from a rectangular or trapezoidal kerf. In addition, the cutting tooth 60 slices through soft tissue, cleaving it radially inward of the luminal wall. Tissue that is positioned radially inward of the kerf rides along the radially inner surface 46 of the primary tissue-removing component 24. When the arcuate portion 72 of the radially inner surface 46 defining the corresponding inner shearing member 62 engages the tissue, it shears the tissue radially inward. Depending on the material properties of the tissue, the tissue might fracture upon engaging the arcuate portion 72 or curl radially inwardly in response to the shearing. The trailing portion 74 of the radially inner surface 46 defining the inner shearing member 62 impacts any tissue located at a sufficiently radially inward position for engagement therewith at an obtuse angle, which causes further shearing of the tissue. Preferably, the impact between the trailing portion 74 of the radially inner surface 46 and the tissue causes the tissue to fracture or otherwise break away from the body lumen for removal therefrom. With continued axial advancement of the catheter 2 and rotation of the tissue-removing element 4, the adjacent trailing secondary tissue-removing component 26 subsequently engages the tissue in much the same way as the cutting tooth 60 of the primary tissue-removing component 24. Thereafter, an adjacent primary tissue-removing component 24 engages the tissue, as disclosed above.

Figure 13:
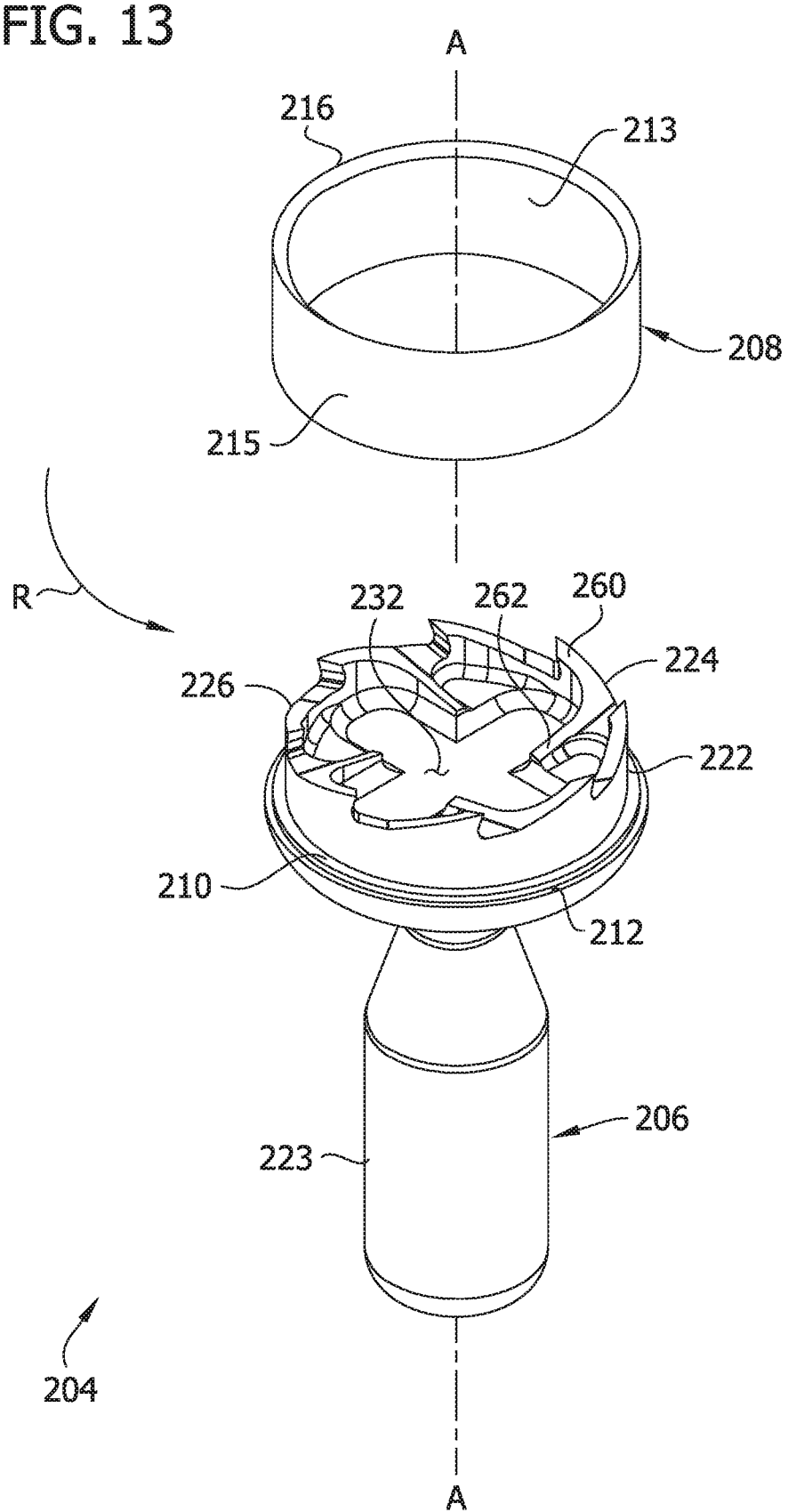
FIG. 13 is an exploded perspective of another embodiment of a tissue-removing element.
Figure 14:
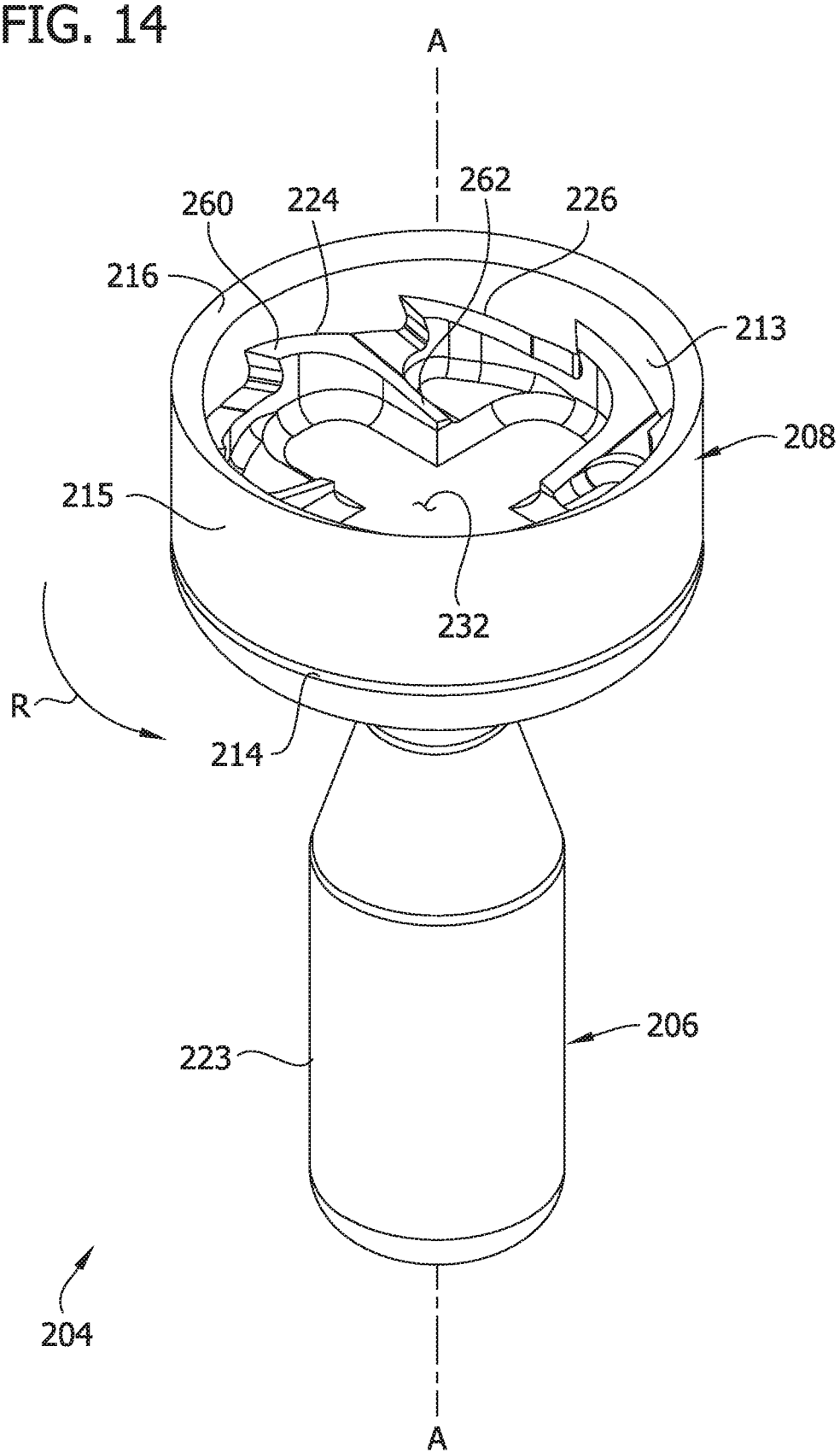
FIG. 14 is a perspective of the tissue-removing element of FIG. 13.

Referring to FIGS. 13 and 14, another embodiment of a tissue-removing element is generally indicated at reference numeral 204. Unlike the tissue-removing element 4, the tissue-removing element 204 is a two-piece assembly. The tissue-removing element 204 includes a tissue-removing element body generally indicated at 206 and an annular cutting blade generally indicated at 208. The tissue-removing element body 206 is configured to be connected to the driveshaft 12 for rotation about an axis of rotation A in a cutting direction R. The cutting blade 208 is fixedly mounted on the body 206 for mutual rotation therewith. As will be discussed in further detail below, features of the cutting blade 208 and tissue-removing element body 206 operate together to engage and remove tissue from a body lumen as the tissue-removing element 204 rotates in the cutting direction R and advances (e.g., moves) distally through the body lumen. Though the illustrated tissue-removing element 204 is a two-piece assembly, it is also contemplated that the tissue-removing element 204 could be constructed from one piece or more than two pieces without departing from the scope of the invention.

The illustrated tissue-removing element body 206 has a similar construction to the tissue-removing element 4. The body 206 has opposite distal and proximal ends spaced apart along the axis of rotation A. A stem 223 at the proximal end of the body 206 is configured to be operatively connected to the driveshaft 12 and a tissue-removing head 222 is positioned at the distal end of the body. In one or more embodiments, the one-piece tissue-removing element body 206 can be made from one of 465 stainless steel, 17-4 stainless steel, MP35N alloy, 35N LT alloy, titanium, and blends thereof. Other materials, such as other types of stainless steel, tool steel, nickel, cobalt, chromium molybdenum, plastic, or combinations thereof, can also be used without departing from the scope of the invention.

Like the tissue-removing head 22, the tissue-removing head 222 comprises four primary tissue-removing components 224 and four secondary tissue-removing components 226. Thus, as discussed above in reference to the tissue-removing element 4, the tissue-removing head 222 defines cutting teeth 260, 226 that are spaced apart from one another around the axis of rotation A. The tissue-removing head 222 also defines inner shearing members 262 (broadly, inner raised elements) disposed radially inward of the cutting teeth 260, 226 and spaced apart from one another around the axis of rotation A. The cutting teeth 260, 226 protrude distally beyond the inner shearing members 262 in the illustrated embodiment. It will be understood that the tissue-removing element body 206 could have other numbers, shapes, and arrangements of cutting teeth and inner raised elements without departing from the scope of the invention. The tissue-removing head 222 defines a depression 232 radially inward of the cutting teeth 260, 226 and inner shearing members 262 for receiving tissue the primary and secondary tissue-removing components 224, 226 remove from the body lumen wall and redirecting the tissue toward the tissue-receiving chamber 30. In general, the teachings of the cutting teeth 260, 226 and inner shearing members 262 set forth above herein apply equally to the present cutting teeth and inner shearing members. However, the cutting teeth could have other designs and configurations and the shearing members could be raised elements of other designs and configurations without departing from the scope of the invention.

Unlike the tissue-removing element 4, a portion of the tissue-removing element body 206 extends radially outward from the tissue-removing head 222. Referring particularly to FIG. 13, the illustrated tissue-removing element body 206 defines a blade ledge 210 and a weld ledge 212 for mounting the blade 208 on the tissue-removing element body. The blade ledge 210 extends radially outward from the tissue-removing head 222 to define an annular seat oriented substantially perpendicular to the axis of rotation A. The weld ledge 212 extends radially outward from the blade ledge 210 at an axial position that is offset from the blade ledge. In the illustrated embodiment, the weld ledge 212 defines an outer radius of the tissue-removing element body 206 that is about the same as the outer radius of the annular blade 208. As will be discussed in further detail below, the blade ledge 210 is configured to engage and support the annular cutting blade 208 on the tissue-removing element body 206. The weld ledge 212 is configured to define a weld channel 214 (FIG. 14) with the cutting blade for receiving a weld that joins the blade to the body to form the tissue-removing element 204.

Referring again to FIG. 13, the annular cutting blade 208 has an inner surface 213 facing generally inward toward the axis of rotation A and an outer surface 215 facing generally outward away from the axis of rotation. In one or more suitable embodiments, the cutting blade 208 is made from a harder material than the tissue-removing element body 206 (e.g., tool steels, carbides, ceramics, 465 stainless steel, 17-4 stainless steel, other stainless steels, or cobalt alloys, etc.).

When mounted on the tissue-removing element body 206 as shown in FIG. 14, the cutting blade 208 extends axially along the axis of rotation A from a proximal end that engages the blade ledge 210 to an opposite distal end. A distal end portion of the inner surface 213 is chamfered to define an annular cutting edge 216 at the distal end of the blade 208. In the illustrated embodiment, the cutting edge 216 is a continuous, non-serrated edge. In other embodiments, the cutting edge could be serrated, toothed, etc. without departing from the scope of the invention.

Figure 15:
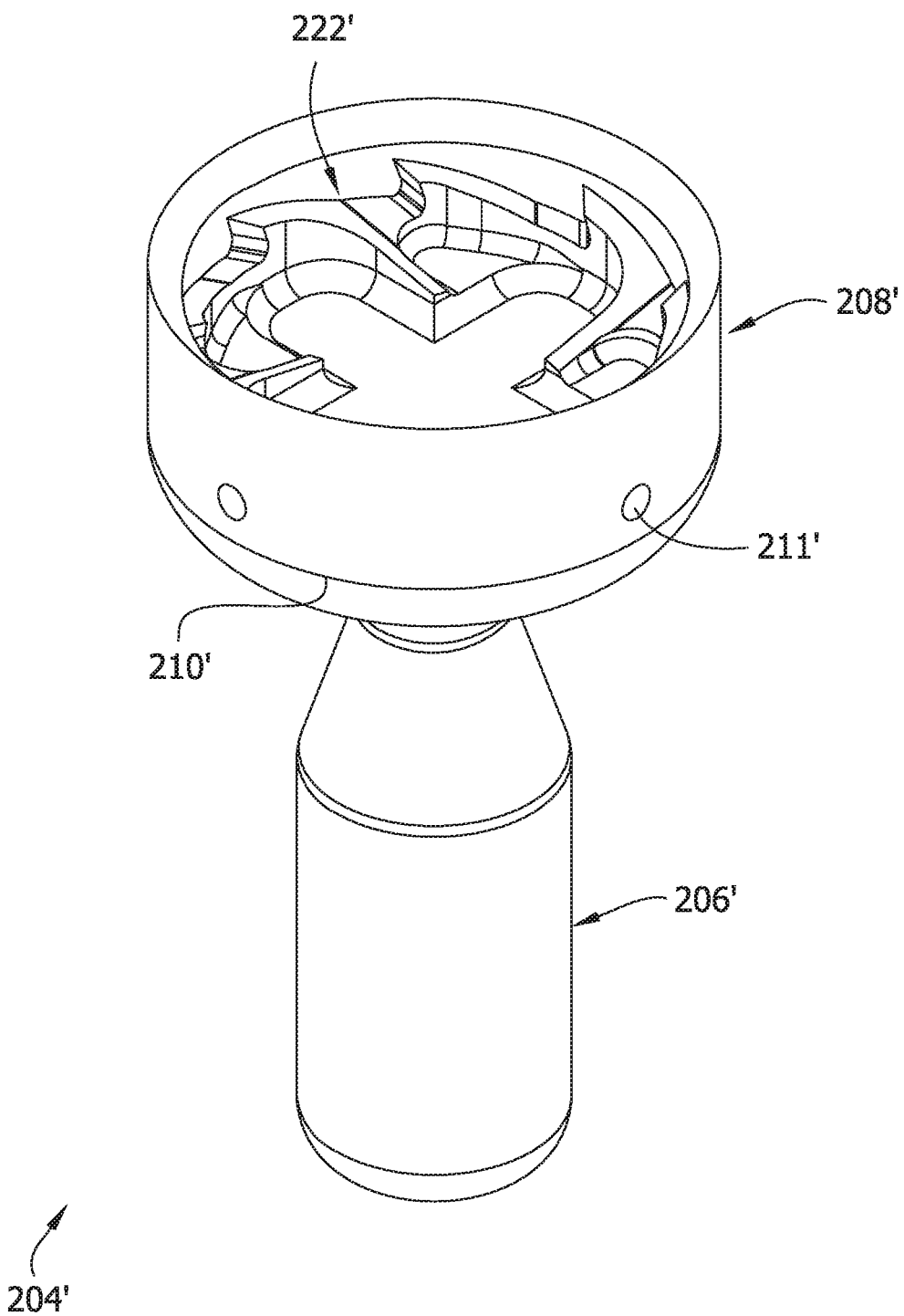
FIG. 15 is a perspective of another embodiment of a tissue-removing element.

When the blade 208 is mounted on the body 206 as shown in FIG. 14, the proximal end of the blade engages the blade ledge 210. A radially outer portion of the blade 208 extends beyond the radially outer edge of the blade ledge 210 and over the weld ledge 212 to define the annular weld channel 214 as shown in FIG. 14. In the illustrated embodiment, the weld channel 214 is configured to be partially or entirely filled with a weld that joins the tissue-removing element body 206 to the annular blade 208 and fixes the blade to the body. The weld channel 214 enables the blade 208 to be welded to the body 206 without forming a weld that protrudes radially outward to interfere with the vessel or atheroma tissue during use. It will be understood that the blade 208 could be joined to the tissue-removing element body 206 in other ways without departing from the scope of the invention. For example, as shown in FIG. 15, in another embodiment of a tissue-removing element 204', the tissue-removing element body 206' forms a blade ledge 210' but no weld ledge. Instead of welding, the annular cutting blade 208' is seated on the blade ledge and pinned (broadly, mechanically fastened) to the tissue-removing element body using pins 211'. For example, in one or more embodiments, the pins 211' extend radially through the cutting blade 208' and into the tissue-removing head 222' to secure the blade to the tissue-removing element body 206'. In another embodiment (not shown) each of the tissue-removing element body and annular blade comprise complementary interlocking features that interlock to mechanically fasten the blade to the body.

As shown in FIG. 14, when the cutting blade 208 is mounted on the tissue-removing element body 206, the annular cutting edge 216 extends around the axis of rotation A at the distal end of the tissue-removing element 204. In the illustrated embodiment, the annular cutting blade 208 protrudes distally beyond the cutting teeth 260, 226 and protrudes distally beyond the inner shearing members 262. The radially inner surface 213 of the annular cutting blade 208 abuts the radially outer surfaces of the cutting teeth 260, 226 such that there is no gap between the cutting blade and the cutting teeth. Optionally, adhesive may be used to fill any remaining gap between the annular cutting blade and the radially outer surfaces of the cutting teeth. In other embodiments, the cutting blade could be spaced apart radially outward from the cutting teeth relative to the axis of rotation without departing from the scope of the invention.

In use, the catheter 2 is inserted into a body lumen. The tissue-removing element 204 is deployed adjacent tissue in the body lumen, the driveshaft 12 rotates the tissue-removing element around the axis of rotation A in the cutting direction R, and the catheter 2 advances through the body lumen until the tissue-removing element engages the tissue. As the tissue-removing element 204 rotates, the cutting edge 216 of the annular cutting blade 208 forms a first cut in the tissue and the cutting teeth 260, 262 form a second cut in the tissue radially inward of the first cut. The cutting edge 216 continuously engages the tissue in the first cut, and it is believed that this helps prevent the tissue-removing element 204 from disengaging from the tissue. The cutting teeth 260, 226 cut tissue positioned radially inward of the first cut to prevent the tissue-removing element from bottoming out against the tissue. In addition, the inner shearing members 262 engage the tissue radially inward of the second cut to shear the tissue toward the depression 32, which redirects the tissue toward the tissue-collection chamber 30 of the catheter 2 for subsequent disposal.

In one suitable method of making the tissue-removing element 2, the tissue-removing element body 206 is formed separately from the annular cutting blade 208. In one embodiment, the tissue-removing element body 206 is machined from a one-piece blank using a multi-axis mill or Swiss machine. The annular cutting blade 208 is formed by cutting a hypotube to length and grinding at least a radially inner surface of the hypotube member to form the cutting edge 216. After forming the cutting edge 216, the annular cutting blade 208 is positioned over the tissue-removing element body 206 so that the proximal end of the blade engages the blade ledge 210 and the radially inward surface of the blade engages the radially outer surfaces of the cutting teeth 260, 226. The cutting blade 208 is then welded to the tissue-removing element body 206 such that the weld fills the weld channel 214. Of course, in the embodiment illustrated in FIG. 15, the blade 208' is pinned to the body 206'. In still other embodiments, the cutting blade may be both welded and pinned, or it may be rotationally affixed using complementary interlocking features.

Figure 16:
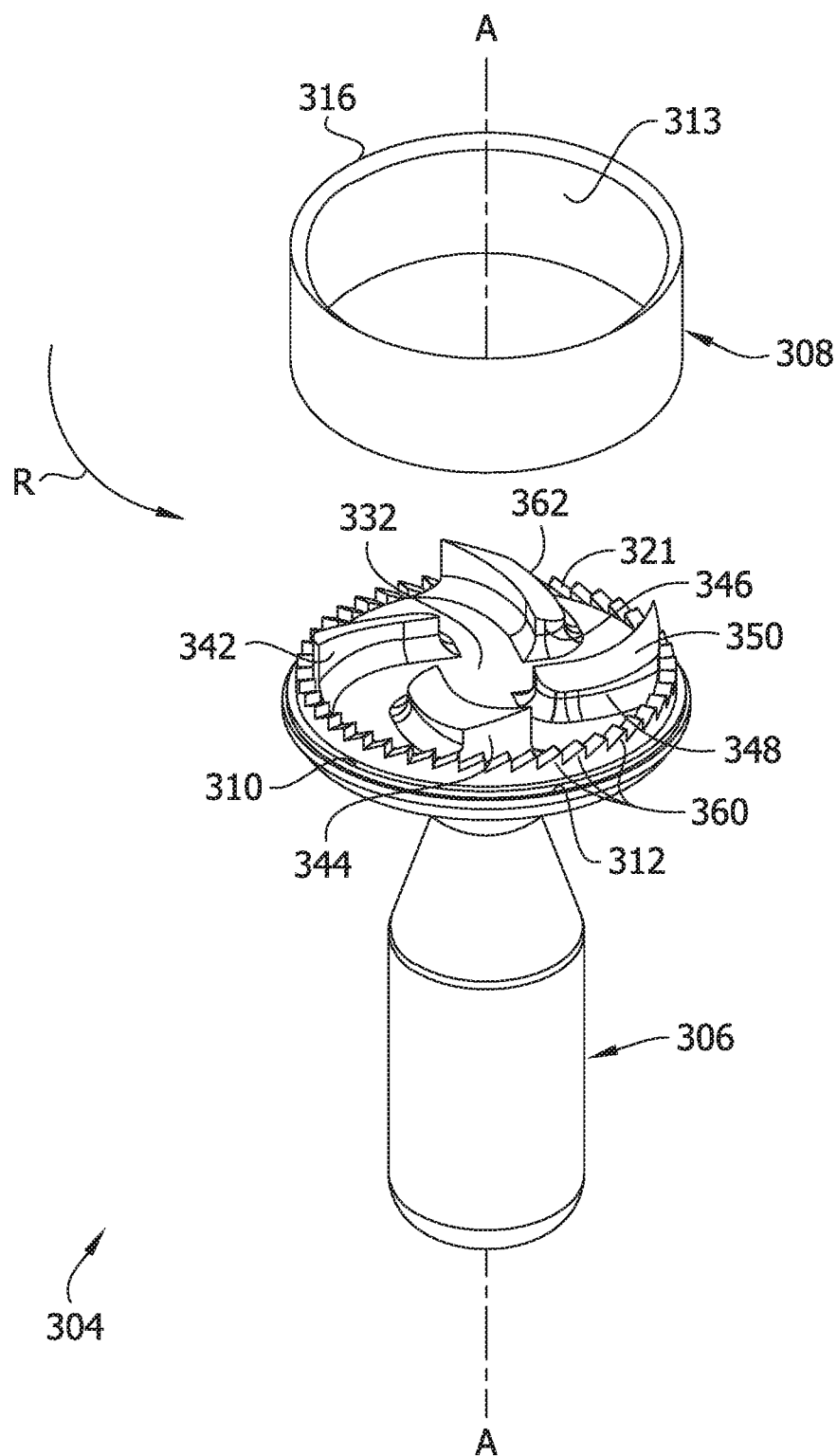
FIG. 16 is an exploded perspective of another embodiment of a tissue-removing element.
Figure 17:
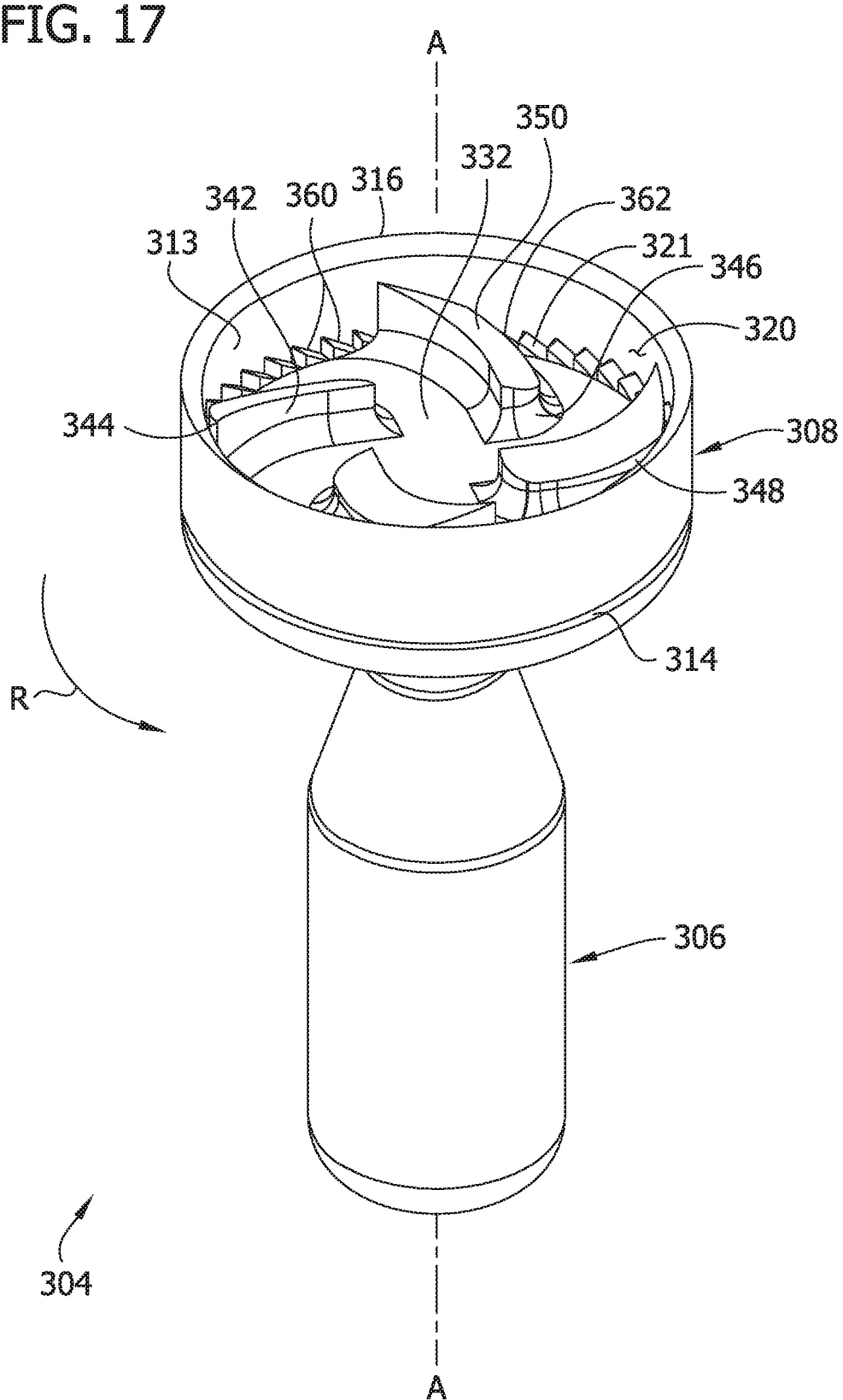
FIG. 17 is a perspective of the tissue-removing element of FIG. 16.

Referring to FIGS. 16 and 17, another embodiment of a two-piece tissue-removing element is generally indicated at reference number 304. The tissue-removing element 304 is substantially similar to the tissue-removing element 204 except for the differences that are, in part, apparent and, in part, pointed out hereinafter. Features of the tissue-removing element 304 are given the same reference numbers as corresponding features of the tissue-removing element 204, plus 100. Like the tissue-removing element 204, the tissue-removing element 304 includes a tissue-removing element body 306 and an annular cutting blade 308. The annular cutting blade 308 is substantially identical to the cutting blade 208, having an inner surface 313 that defines a continuous annular cutting edge 316. The annular cutting blade 308 is configured to be mounted on the tissue-removing element body 306 for mutual rotation therewith. The tissue-removing element body 306 is configured for operative connection to the driveshaft 12 to rotate the tissue-removing element 304 about an axis of rotation A in a cutting direction R.

In the illustrated embodiment, the tissue-removing element body 306 has a distal end and a proximal end spaced apart along the axis of rotation A. The distal end includes a substantially planar axial end surface 332. Four inner shearing members 362 spaced angularly about the axis of rotation A extend generally axially in the distal direction from the axial end surface 332. Each inner shearing member 362 includes a leading surface 342, radially outer surface 344, radially inner surface 346, trailing surface 348, and axial end surface 350. In this embodiment, the inner shearing members 362 project independently from the surface 332 without being integrally formed with a cutting tooth. That is, the leading, outer, inner, trailing, and axial end surfaces 342, 344, 346, 348, 350 define the shape of the shearing member 362 and no other component of the tissue-removing element body 306. In use, the leading surface 342 of each inner shearing member 362 leads the trailing surface 348 as the tissue removing element body 306 rotates in the cutting direction R. Like the shearing members 62 of the tissue-removing element 4 illustrated in FIGS. 4-12, the leading surface 342 of the shearing members 362 is shaped and arranged to shear tissue radially inward toward the axis of rotation A as the tissue-removing element 340 rotates in the cutting direction R and advances distally through the body lumen. The inner surfaces 346 of the shearing members and the axial end surface 332 of the tissue-removing element body 306 define a depression for redirecting removed tissue toward the tissue-collection chamber 12 as the tissue-removing element 304 rotates in the cutting direction R in use. The shearing members may be of other configurations without departing from the scope of the invention.

A portion of the tissue-removing element body 306 extends radially outward of the inner shearing members 362. Just outside of the inner shearing members 362 relative to the axis of rotation A, the tissue-removing element body 306 includes a generally distally facing surface 321 that defines a ring of cutting teeth 360 surrounding the inner shearing members 362 that are spaced apart from one another around the axis of rotation. The cutting teeth 360 extend axially relative to the flat surface 332 of the tissue-removing element body 304, but the inner shearing members 362 protrude distally beyond the cutting teeth. Radially outward of the cutting teeth 360, the distal end of the tissue-removing element body 306 defines an annular blade ledge 310 defines a generally distally facing seat for securing the annular cutting blade 308 to the body. Like the tissue-removing element body 206, the tissue-removing element body 306 also includes an annular weld ledge 312 that defines a weld channel 314 (FIGS. 17 and 18) for receiving a weld which joins the blade 308 to the body. As with the tissue-removing element 204, the tissue-removing blade 308 could be fastened to the tissue-removing element body 306 in other ways without departing from the scope of the invention.

Figure 18:
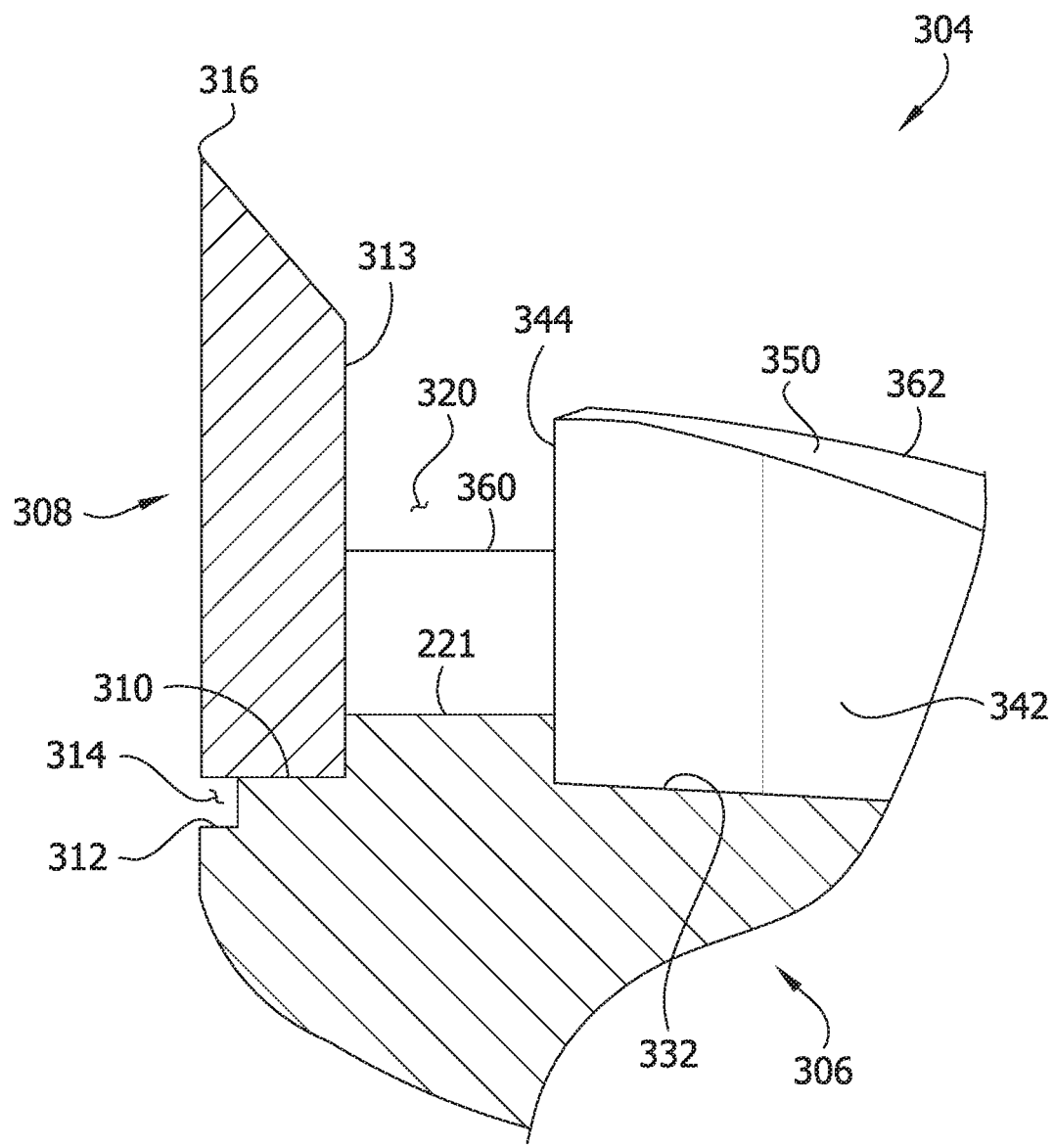
FIG. 18 is a fragmentary section of the tissue-removing element of FIG. 16.

When the annular cutting blade 308 is mounted on the tissue-removing element body 306 as illustrated in FIGS. 17 and 18, the inner shearing members 362 are spaced radially inward of the inner surface 313 blade 308 relative to the axis of rotation A. The outer surface 344 of the inner shearing members 362 are spaced radially inward and oriented in generally opposing relationship with the inner surface 313 of the annular cutting blade 308 to define an annular tissue-receiving channel 320 that extends around the axis of rotation A. The surface 321 that defines the cutting teeth 360 extends between the outer surface 344 of the inner shearing members 362 and the inner surface 313 of the annular cutting blade 308 and forms the bottom surface of the tissue-receiving channel 320. In the illustrated embodiment, the bottom surface 221 of the channel 320 defines teeth 360 that have a rectangular kerf that extends the entire radial width of the channel. But it will be understood that the bottom surface could define teeth or other tissue-removing formations of other shapes, numbers, and/or arrangements, (e.g., teeth that extend less than the entire radial width of the channel) without departing from the scope of the invention. Moreover, the bottom surface of the channel could be substantially flat without departing from the scope of the invention.

In use, the catheter 2 is inserted into a body lumen. The tissue-removing element 304 is deployed adjacent tissue in the body lumen, the driveshaft 12 rotates the tissue-removing element around the axis of rotation A in the cutting direction R, and the catheter 2 advances through the body lumen until the tissue-removing element engages the tissue. As the tissue-removing element 304 rotates, the cutting edge 316 of the annular cutting blade 308 forms a first cut in the tissue. Tissue positioned radially inward of the first cut is received in the tissue-receiving channel 320. The tissue received in the channel 320 provides a structure for the cutting edge 316 to continuously engage. As the catheter 2 advances axially through the body lumen, some of the tissue engaging the inner surface 313 of the cutting blade 308 travels proximally through the channel 320. When the tissue reaches the axial depth of the cutting teeth 360, the teeth engage the tissue in the tissue-receiving channel 320 to form a second cut in the tissue radially inward of the first cut relative to the axis of rotation A. The second cut prevents the tissue-removing element from bottoming out against the tissue, which would inhibit the cutting blade 308 from advancing axially as it rotates through the first cut. The inner shearing members 362 engage tissue positioned radially inward of the cutting teeth 360 and the second cut and shear the tissue radially inward. The inner surfaces 346 of the shearing members 362 and axial end surface 332 of the tissue-removing element body redirect the sheared tissue toward the tissue-collection chamber 30 of the catheter 2 for subsequent disposal.

Where dimensional ranges are cited in the present disclosure, it should be understood that the range is inclusive of the end points of the range, unless otherwise indicated. For example, a range of "between about 1 inch and about 2 inches" includes lengths of about 1 inch and about 2 inches and all of the lengths between those two end points of the range.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue from a body lumen, the tissue-removing catheter comprising: a rotatable driveshaft; and a tissue-removing element coupled to the rotatable driveshaft for rotating the tissue-removing element in a cutting direction about an axis of rotation, the tissue-removing element having opposite first and second axial ends, the tissue-removing element including an annular cutting blade having a continuous cutting edge extending around the axis of rotation at the first axial end of the tissue-removing element, and primary tissue-removing components at the first axial end of the tissue-removing element spaced apart from one another around the axis of rotation and disposed radially inward of the cutting edge relative to the axis of rotation, each primary tissue-removing component having a leading surface extending generally axially, a radially outer surface extending generally axially, a radially inner surface extending generally axially and generally inward relative to the axis of rotation from adjacent a leading end toward a trailing end thereof, and an axial end surface intersecting the leading, the radially outer, and the radially inner surfaces at respective leading, radially outer, and radially inner edges, wherein the leading surface, the leading edge and leading portions of the radially outer surface, the radially inner surface, and the axial end surface of each primary tissue-removing component at least partially define a cutting tooth adapted to cut tissue as the tissue-removing element rotates to facilitate removal of tissue, wherein trailing portions of the radially outer surface, the radially inner surface, and the axial end surface of each primary tissue-removing component at least partially define an inner shearing member adapted to impact tissue and shear the impacted tissue radially inwardly as the tissue-removing element rotates to facilitate removal of hard tissue, wherein the annular cutting blade and the primary tissue-removing components are fixed with respect to one another; and wherein the leading surface of each primary tissue-removing component intersects the respective radially inner surface at an intermediate edge, wherein at least a portion of the inner shearing member is located radially inward of the intermediate edge, wherein the radially inner surface extends contiguously from the intermediate edge to the trailing end thereof, and wherein said at least a portion of the inner shearing member located radially inward of the intermediate edge is partially defined by the radially inner surface.

2. A tissue-removing catheter as set forth in claim 1, wherein the cutting edge of the annular cutting blade protrudes axially beyond the primary tissue-removing components.

3. A tissue-removing catheter as set forth in claim 1, wherein a radially inner surface of the annular cutting blade abuts radially outer surfaces of the cutting teeth defined by the primary tissue-removing components.

4. A tissue-removing catheter as set forth in claim 1, further comprising a central depression formed in the first axial end of the tissue-removing element radially inward of the cutting teeth defined by the primary tissue-removing components.

5. A tissue-removing catheter as set forth in claim 1, wherein the annular cutting blade is configured to form a first cut in the tissue and the cutting teeth defined by the primary tissue-removing components are configured to form a second cut in the tissue as the tissue removing catheter rotates about the axis of rotation in the body lumen.

6. A tissue-removing catheter as set forth in claim 1, wherein the annular cutting blade is mechanically fastened to the primary tissue-removing components.

7. A tissue-removing catheter as set forth in claim 1, wherein the annular cutting blade is welded to the primary tissue-removing components.

8. A tissue-removing catheter as set forth in claim 1, wherein the annular cutting blade is pinned to the primary tissue-removing components.

9. A tissue-removing catheter as set forth in claim 1, wherein the cutting tooth and the inner shearing member of each primary tissue-removing component are integrally formed as a single piece of material.

10. A tissue-removing catheter as set forth in claim 1, wherein the radially inner surface of each primary tissue-removing component has an arcuate portion curving inward relative to the axis of rotation from adjacent the leading end toward the trailing end thereof.

11. A tissue-removing catheter set forth in claim 1, further comprising a plurality of secondary cutting components at the first axial end of the body and spaced apart from one another around the axis of rotation, each secondary cutting component being disposed between adjacent primary tissue-removing components and having a leading surface extending generally axially, a radially outer surface extending generally axially, a radially inner surface extending generally axially and generally inward relative to the axis of rotation from adjacent a leading end toward a trailing end thereof, and an axial end surface intersecting the leading, the radially outer, and the radially inner surfaces at respective leading, radially outer, and radially inner edges, wherein the leading surface, the leading edge, and leading portions of the radially outer surface, the radially inner surface, and the axial end surface at least partially forms a cutting tooth adapted to cut tissue as the tissue-removing element rotates to facilitate removal of tissue.

* * * * *